US011260209B2

(12) United States Patent
Siciliano

(10) Patent No.: US 11,260,209 B2
(45) Date of Patent: Mar. 1, 2022

(54) PEN STYLE MICRONEEDLING MACHINE APPARATUS

(71) Applicant: FK Irons, Inc., Doral, FL (US)

(72) Inventor: Gaston Siciliano, Miami, FL (US)

(73) Assignee: FK Irons Inc., Doral, FL (US)

( * ) Notice: Subject to any disclaimer, the term of this patent is extended or adjusted under 35 U.S.C. 154(b) by 413 days.

(21) Appl. No.: 16/115,666

(22) Filed: Aug. 29, 2018

(65) Prior Publication Data

US 2018/0369553 A1  Dec. 27, 2018

Related U.S. Application Data

(63) Continuation-in-part of application No. 29/639,722, filed on Mar. 8, 2018, now Pat. No. Des. 865,965, and a continuation-in-part of application No. 15/245,336, filed on Aug. 24, 2016, now Pat. No. 10,744,312.

(51) Int. Cl.
*A61B 17/34* (2006.01)
*A61M 37/00* (2006.01)
*A61B 17/00* (2006.01)

(52) U.S. Cl.
CPC ..... *A61M 37/0015* (2013.01); *A61B 17/3476* (2013.01); *A61M 37/0076* (2013.01); *A61B 2017/00398* (2013.01); *A61B 2017/00407* (2013.01); *A61M 2037/0023* (2013.01)

(58) Field of Classification Search
CPC ...... A61M 2037/0023; A61M 37/0076; A61B 17/3476; A61B 2017/00398; A61B 2017/00407

USPC .......................................................... 81/9.22
See application file for complete search history.

(56) References Cited

U.S. PATENT DOCUMENTS

| 2,588,623 | A | | 3/1952 | Eliscu |
| D226,829 | S | | 5/1973 | Staub |
| D229,869 | S | | 1/1974 | Staub |
| D241,475 | S | | 9/1976 | Staub |
| 4,137,632 | A | * | 2/1979 | Pfanzer ............... B23D 49/162 30/393 |
| D254,150 | S | | 2/1980 | Barton |
| D288,359 | S | | 2/1987 | Hoff |
| 4,644,952 | A | | 2/1987 | Papita |
| 4,647,260 | A | | 3/1987 | O'Hara |
| 4,665,912 | A | * | 5/1987 | Burton .................... A61F 9/007 606/185 |

(Continued)

FOREIGN PATENT DOCUMENTS

| CN | 102469867 | 5/2012 |
| CN | 202682550 | 1/2013 |

(Continued)

*Primary Examiner* — Joseph J Hail
*Assistant Examiner* — Arman Milanian
(74) *Attorney, Agent, or Firm* — Akerman LLP; Peter A. Chiabotti; Roy Zachariah

(57) ABSTRACT

A microneedling machine for tattooing is disclosed, which has a substantially radially symmetric exterior shape and may include subcomponents that can be disassembled and sterilized. The machine may include an adjustment mechanism for configuring the impact of the microneedle into skin. The machine may also include a motion translation device adapted to change rotational motion of the drive shaft or motor into linear reciprocating motion of the microneedle.

19 Claims, 12 Drawing Sheets

(56) References Cited

U.S. PATENT DOCUMENTS

| | | | |
|---|---|---|---|
| 4,719,825 A * | 1/1988 | LaHaye | A01K 11/005 222/390 |
| D294,388 S | 2/1988 | Hardy | |
| D294,519 S | 3/1988 | Hardy | |
| 4,796,624 A * | 1/1989 | Trott | A61M 37/0084 215/247 |
| 5,032,043 A | 7/1991 | Hollifield | |
| 5,279,552 A * | 1/1994 | Magnet | A61M 37/0076 604/47 |
| 5,341,704 A | 8/1994 | Klemm | |
| 5,380,132 A | 1/1995 | Parks | |
| D364,923 S | 12/1995 | Chou | |
| 5,586,473 A | 12/1996 | Chou | |
| 5,601,387 A | 2/1997 | Sanford | |
| D380,046 S | 6/1997 | Domanowski | |
| D389,578 S | 1/1998 | Emerson | |
| D389,915 S | 1/1998 | Emerson | |
| 5,776,158 A | 7/1998 | Chou | |
| 6,033,421 A * | 3/2000 | Theiss | A61M 37/0076 606/186 |
| D433,752 S | 11/2000 | Saravia | |
| D434,149 S | 11/2000 | Mirhashemi | |
| D439,337 S | 3/2001 | Jones | |
| D440,310 S | 4/2001 | Laks | |
| D448,483 S | 9/2001 | Behnke | |
| D453,833 S | 2/2002 | Hess | |
| D457,955 S | 5/2002 | Bilitz | |
| D465,279 S | 11/2002 | Etter | |
| 6,505,530 B2 * | 1/2003 | Adler | A45D 34/04 30/362 |
| D490,152 S | 5/2004 | Myall | |
| D493,530 S | 7/2004 | Reschke | |
| D493,532 S | 7/2004 | Levaughn | |
| 6,772,656 B2 | 8/2004 | Godoy | |
| D521,641 S | 5/2006 | Reschke | |
| D535,396 S | 1/2007 | Reschke | |
| D536,451 S | 2/2007 | Haydu | |
| D538,934 S | 3/2007 | Wilkinson | |
| D538,936 S | 3/2007 | Bohmel | |
| 7,211,097 B2 | 5/2007 | Carrasco | |
| 7,225,708 B2 | 6/2007 | Chen | |
| D549,325 S | 8/2007 | Schnitzler | |
| D549,779 S | 8/2007 | Shimizu | |
| D560,803 S | 1/2008 | Tasse | |
| 7,335,211 B2 | 2/2008 | Chen | |
| 7,337,697 B2 | 3/2008 | Bader | |
| D575,343 S | 8/2008 | Cetera | |
| D581,530 S | 11/2008 | Thierfelder | |
| D582,981 S | 12/2008 | Bhavnani | |
| D586,465 S | 2/2009 | Faulkner | |
| D597,668 S | 8/2009 | Woodruff | |
| D612,051 S | 3/2010 | Ruf | |
| D621,042 S | 8/2010 | Ruf | |
| D622,000 S | 8/2010 | Kluge | |
| 7,810,414 B2 | 10/2010 | Hsu | |
| D628,293 S | 11/2010 | Ruf | |
| D628,695 S | 12/2010 | Ruf | |
| D634,426 S | 3/2011 | Zollers | |
| D638,939 S | 5/2011 | Eikhoff | |
| D645,965 S | 9/2011 | Muto | |
| D664,657 S | 7/2012 | Vieira | |
| D667,554 S | 9/2012 | Casabonne | |
| D677,790 S | 3/2013 | Little | |
| D679,396 S | 4/2013 | Jan | |
| D691,263 S | 10/2013 | Chen | |
| 8,771,308 B2 * | 7/2014 | Lin | F16H 21/50 606/186 |
| 8,794,109 B2 * | 8/2014 | Lee | A61M 37/0084 81/9.22 |
| 8,920,379 B2 | 12/2014 | Lee | |
| D723,685 S | 3/2015 | Myers | |
| 9,050,445 B2 | 6/2015 | Klebs | |
| D736,915 S | 8/2015 | Schultz | |
| D737,441 S | 8/2015 | Presser | |
| D737,972 S | 9/2015 | Chen | |
| 9,126,027 B2 | 9/2015 | Lin | |
| D743,546 S | 11/2015 | Jayaraj | |
| D745,152 S | 12/2015 | Mayer | |
| D750,243 S | 2/2016 | Tetzlaff | |
| D750,258 S | 2/2016 | Crossley | |
| 9,259,561 B2 | 2/2016 | Lee | |
| D762,303 S | 7/2016 | Jayaraj | |
| 9,393,395 B2 | 7/2016 | Miller | |
| D763,443 S | 8/2016 | Chen | |
| D765,841 S | 9/2016 | Schuerg | |
| D765,842 S | 9/2016 | Schuerg | |
| D766,432 S | 9/2016 | Schuerg | |
| 9,504,814 B2 | 11/2016 | Frister | |
| D779,670 S | 2/2017 | Kryslyniak | |
| D781,419 S | 3/2017 | Bojanowski | |
| D782,041 S | 3/2017 | Pell | |
| D782,667 S | 3/2017 | Fuhr | |
| D785,795 S | 5/2017 | Amano | |
| 9,662,483 B2 | 5/2017 | Sicilano | |
| D791,946 S | 7/2017 | Schwartz | |
| D791,947 S | 7/2017 | Chen | |
| 9,707,385 B1 | 7/2017 | Chen | |
| D794,192 S | 8/2017 | Schuerg | |
| D794,193 S | 8/2017 | Schuerg | |
| D794,194 S | 8/2017 | Schuerg | |
| D803,398 S | 11/2017 | Israni | |
| D805,195 S | 12/2017 | Lee | |
| D805,196 S | 12/2017 | Lee | |
| D805,197 S | 12/2017 | Lee | |
| D805,198 S | 12/2017 | Lee | |
| D805,640 S | 12/2017 | Lee | |
| D815,738 S | 4/2018 | Ye | |
| D819,207 S | 5/2018 | Blank | |
| D831,208 S | 10/2018 | Benisty | |
| D837,371 S | 1/2019 | Zu | |
| D837,372 S | 1/2019 | Zu | |
| D839,425 S | 1/2019 | Zanata | |
| 10,449,346 B2 | 10/2019 | Juan | |
| 2003/0195542 A1 * | 10/2003 | Lee | A61M 37/0076 606/186 |
| 2005/0055042 A1 | 3/2005 | Carrasco | |
| 2006/0020283 A1 | 1/2006 | Lisec | |
| 2008/0287978 A1 * | 11/2008 | Hickman, III | A61M 37/0076 606/186 |
| 2008/0306502 A1 | 12/2008 | Lisec | |
| 2010/0036317 A1 | 2/2010 | Dginski | |
| 2011/0048174 A1 * | 3/2011 | Lin | A61M 37/0084 81/9.22 |
| 2012/0041374 A1 * | 2/2012 | Lee | A61M 37/0076 604/173 |
| 2012/0123462 A1 * | 5/2012 | Lee | A61M 37/0076 606/185 |
| 2012/0179134 A1 | 7/2012 | Garitano | |
| 2012/0279330 A1 | 11/2012 | Lin | |
| 2013/0123825 A1 | 5/2013 | Demjanenko | |
| 2014/0018835 A1 | 1/2014 | Scherkowski | |
| 2014/0094837 A1 | 4/2014 | Danenberg | |
| 2014/0358172 A1 * | 12/2014 | Lin | A61M 37/0076 606/185 |
| 2014/0358173 A1 | 12/2014 | Lin | |
| 2015/0025561 A1 | 1/2015 | La Fontaine | |
| 2015/0202420 A1 | 7/2015 | Miller | |
| 2015/0352346 A1 | 12/2015 | Webb | |
| 2015/0367118 A1 | 12/2015 | Scherkowski | |
| 2016/0038176 A1 | 2/2016 | Smith | |
| 2016/0074646 A1 | 3/2016 | Norman | |
| 2016/0121093 A1 | 5/2016 | Fan | |
| 2016/0263365 A1 | 9/2016 | Smith | |
| 2016/0354592 A1 | 12/2016 | Juan | |
| 2017/0007814 A1 | 1/2017 | Chan | |
| 2017/0014609 A1 | 1/2017 | Spadoni III | |
| 2017/0065807 A1 | 3/2017 | Niven | |
| 2017/0072177 A1 | 3/2017 | Oscar | |
| 2017/0157382 A1 | 6/2017 | Siciliano | |
| 2017/0173319 A1 | 6/2017 | McGuire | |
| 2017/0354810 A1 | 12/2017 | O'Brien | |
| 2018/0056054 A1 | 3/2018 | Siciliano | |
| 2018/0289902 A1 | 10/2018 | Xiang | |

(56) References Cited

U.S. PATENT DOCUMENTS

| | | |
|---|---|---|
| 2018/0360487 A1 | 12/2018 | Algeri |
| 2018/0369553 A1 | 12/2018 | Siciliano |
| 2019/0134371 A1 | 5/2019 | Johansson |

FOREIGN PATENT DOCUMENTS

| | | | | |
|---|---|---|---|---|
| CN | 203790439 | | 8/2014 | |
| CN | 204411493 | | 6/2015 | |
| CN | 204411493 U | * | 6/2015 | ........ A61M 37/0076 |
| DE | 102016008546 | | 9/2016 | |
| EP | 2944349 | | 11/2015 | |
| FR | 2747927 | | 10/1997 | |
| FR | 2747928 | | 10/1997 | |
| KR | 20090131673 | | 12/2009 | |
| KR | 100973628 | | 8/2010 | |
| KR | 100973628 B1 | * | 8/2010 | ........ A61M 37/0076 |
| KR | 20120000522 | | 1/2012 | |
| KR | 200466520 | | 4/2013 | |
| KR | 20130116095 | | 10/2013 | |
| KR | 101395100 B1 | * | 5/2014 | ........ A61M 37/0084 |
| KR | 20150009459 | | 1/2015 | |
| KR | 101593639 B1 | * | 2/2016 | ........ A61M 37/0076 |
| KR | 20170044510 | | 4/2017 | |
| KR | 20170044510 A | * | 4/2017 | ........ A61M 37/0076 |
| RU | 2270040 | | 2/2006 | |
| WO | 2010120111 | | 10/2010 | |
| WO | 2014202055 | | 12/2014 | |
| WO | 2015094041 | | 6/2015 | |
| WO | 2015160370 | | 10/2015 | |
| WO | 2016159465 | | 10/2016 | |

* cited by examiner

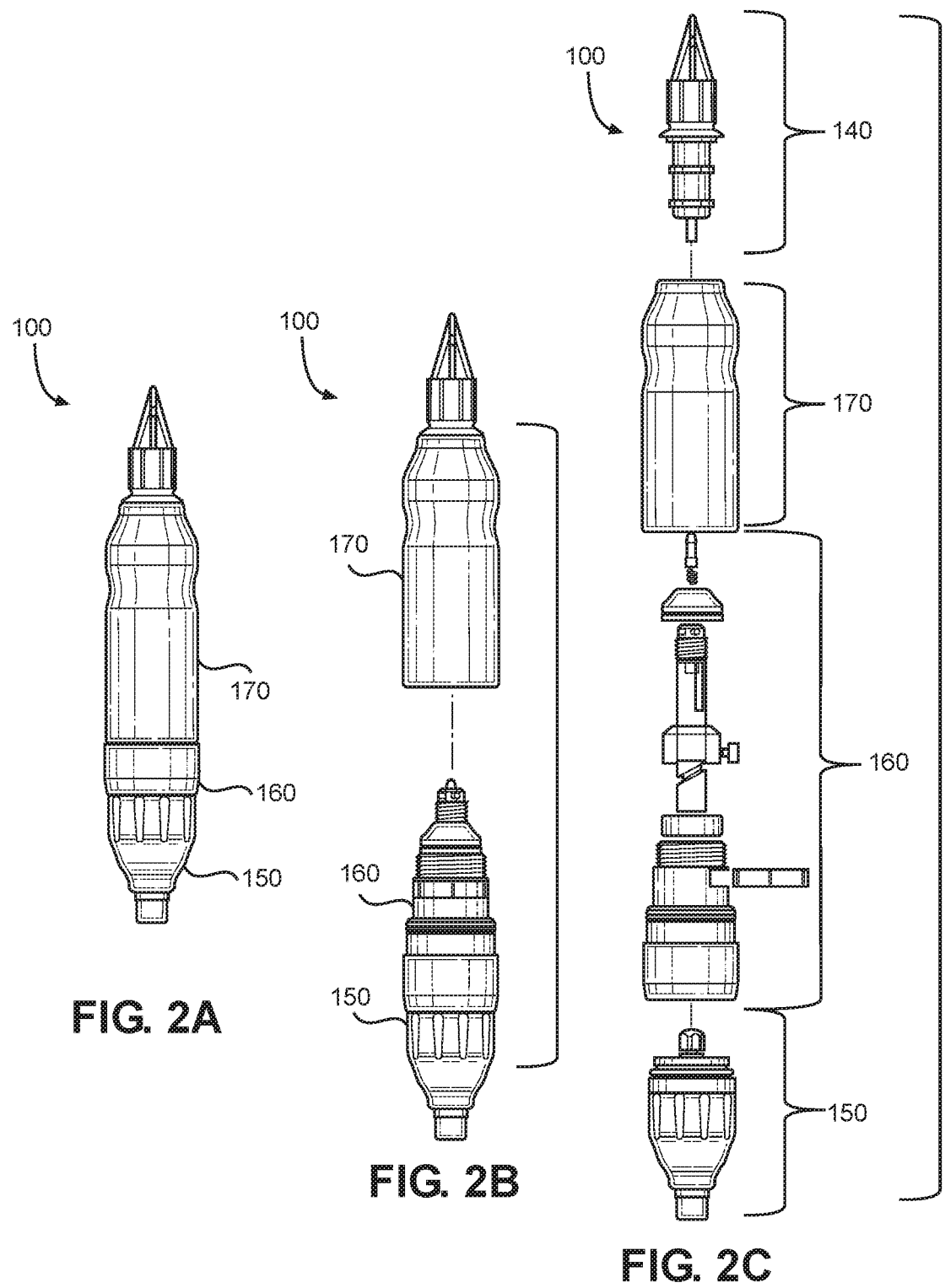

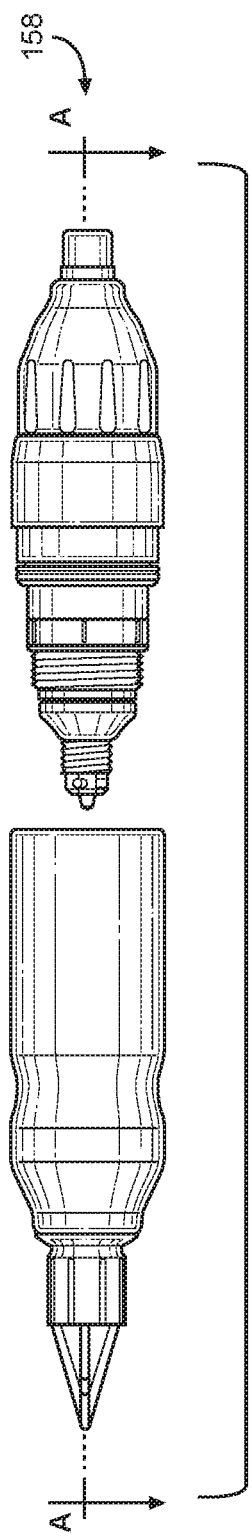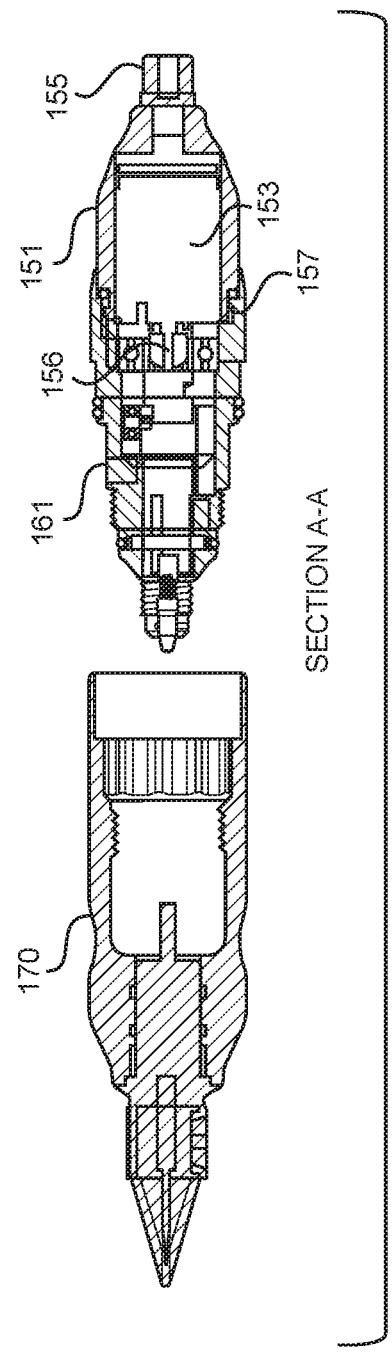
FIG. 3A
FIG. 3B
SECTION A-A

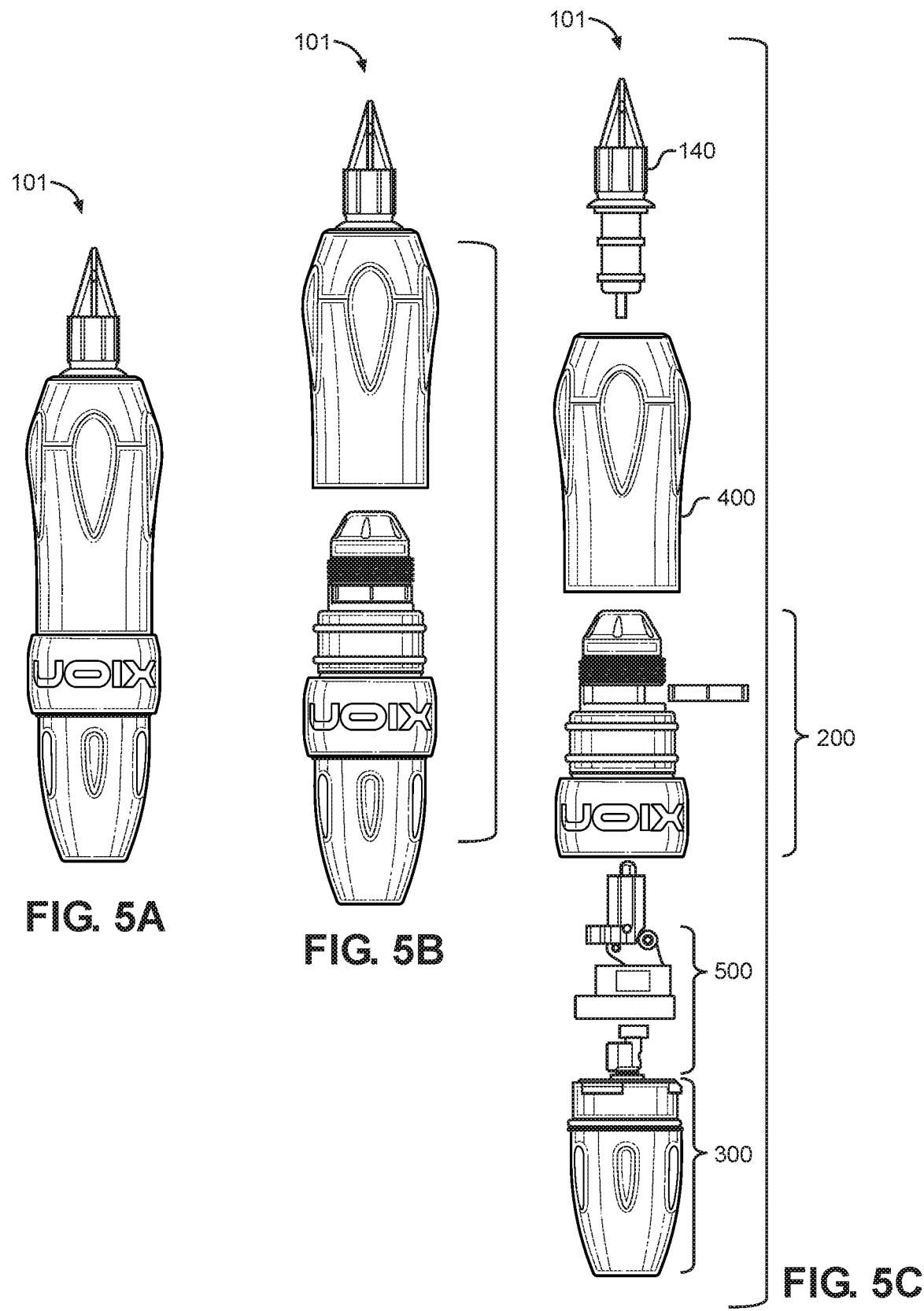

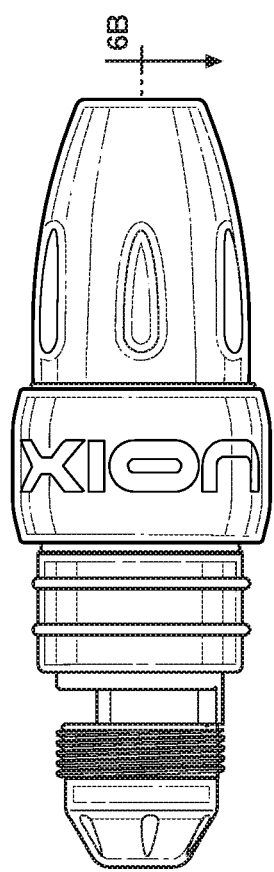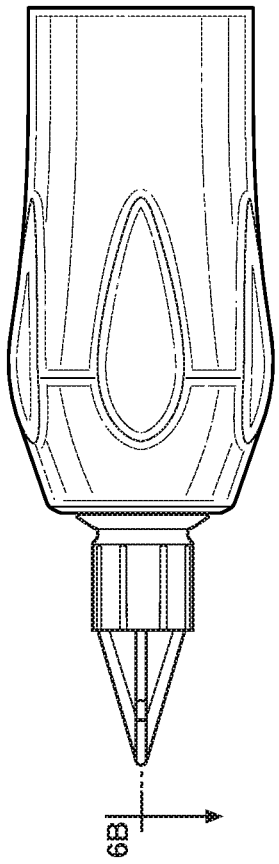
FIG. 6A
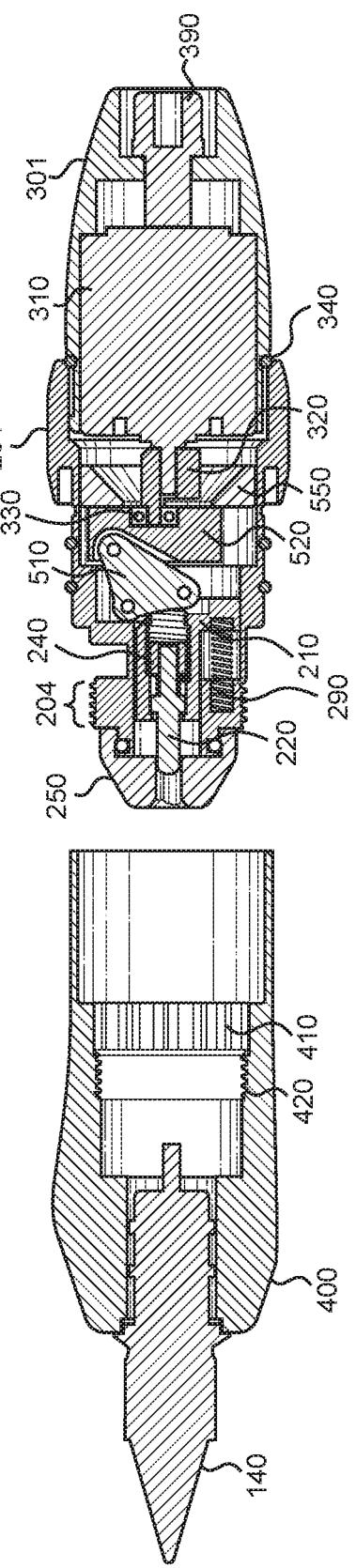
FIG. 6B

PEN STYLE MICRONEEDLING MACHINE APPARATUS

CROSS-REFERENCE TO RELATED APPLICATIONS

The present application claims benefit under 35 U.S.C. Sec. 119 to U.S. utility patent application Ser. No. 15/245,336 filed Aug. 24, 2016, and to U.S. design patent application Ser. No. 29/639,722 filed Mar. 8, 2018. The foregoing applications are hereby incorporated by reference into the present application in their entirety.

BACKGROUND OF THE DISCLOSURE

Field of the Disclosure

The disclosure relates generally to the field of mechanical apparatuses, and more particularly, to a pen style microneedling machine apparatus. Microneedling machines include tattoo machines, permanent makeup machines, and therapeutic skin stimulation machines. When used with hollow needles, they can be useful for implantation of temporary or permanent pigments, compounds, chemicals, large molecules and even cells beneath the skin. They can also be used with non-hollow needles to selectively injure specific layers of skin which stimulate natural healing response.

Background

Tattoo and microneedle machines generally use electric coils to drive a spring-loaded reciprocating needle structure in order to puncture the upper layers of skin and deposit small amounts of colorant into the skin. This type of machine is often bulky, heavy, and cumbersome for the operator (the tattoo artist, skin therapist, or physician), having an off-balance mass relative to the operator's hand, making it more difficult for the operator to re-orient the machine by fingertip in the operator's hand during use. These devices are also prone to overheating and produce vibration, further causing discomfort to the user and thereby shortening the length of time the device can be used over a continuous period. Environmentally for both user and subject, they are inherently noisy during operation, thus leading to aural fatigue and shorter tattooing or therapy sessions.

Due to the nature of the prior designs, which include exposed mechanical components and electrical connections, properly cleaning, sterilizing, or autoclaving the device or its constituent components has been limited or impossible. Using non-sterilizable machines or components creates an inherent health and safety issue for the subject as well as for the operator, or leads to expensive waste in disposing of contaminated parts.

Tattoo artists, cosmetic tattooists, and microneedle therapists desire something that fits more comfortably in their hand and can be manipulated, rotated, and reoriented by fingertip with one hand during use, limit vibration and heat, and that allows them to "paint" or "draw" on a subject's skin with similar comfort to a pen or a pencil.

While other solutions in the art have attempted to provide machines that would be comfortable for operators to use, they tend to fail in one or more respects. In addition to comfort, microneedle operators desire an apparatus that allows for adjustment of the needle stroke—more particularly the length at which the needle protrudes out from the machine during operation—as well as an apparatus that allows for adjustment of the "give" or force at which the needle impacts the target skin.

It would, therefore, be desirable to have a pen style microneedling machine apparatus with adjustable stroke, adjustable give, that is composed of cleanable components, compatible with multiple tattoo needle cartridge systems and grip styles, lightweight, and virtually vibration free.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

In this specification where a document, act, or item of knowledge is referred to or discussed, that reference or discussion is not an admission that the document, act, or item of knowledge or any combination thereof was at the priority date, publicly available, known to the public, part of common general knowledge, or otherwise constitutes prior art under the applicable statutory provision; or is known to be relevant to an attempt to solve any problem with which this specification is concerned.

BRIEF SUMMARY OF THE DISCLOSURE

The following presents a simplified summary of the disclosure in order to provide a basic understanding of some aspects of the disclosure. This summary is not an extensive overview of the disclosure. It is intended neither to identify key or critical elements of the disclosure nor to delineate the scope of the disclosure. Its sole purpose is to present some concepts of the disclosure, in accordance with the disclosure, in a simplified form as a prelude to the more detailed description presented later.

In one embodiment, a microneedle drive apparatus for converting rotational motion into reciprocating oscillating motion is disclosed. The microneedle drive apparatus comprises a housing having substantially radial symmetry about a central axis, a rotary motor having an output driveshaft end where the driveshaft end has an axis of rotation positioned substantially co-axial to the central axis and is constrainable within the housing, and a motion translation device. The motion translation device comprises an offset connectable to the driveshaft end such that the driveshaft end rotatably drives the offset a distance from the central axis in an orbit around the central axis, a follower slidably constrained within the housing and having two faces, and a bellcrank. The first follower face has a groove dimensioned to be engaged by the offset, while the second follower face is adapted to be in mechanical communication with a first arm of the bellcrank. The bellcrank has a fulcrum about which the bellcrank pivots back and forth as it is driven by the follower. As the bellcrank pivots, the second arm of the bellcrank oscillates approximately parallel to the central axis. The end of the second arm reciprocates along an arc, the arc approximately parallel to the central axis and which is capable of operably engaging a microneedle cartridge.

In another embodiment, a microneedle give adjustment apparatus for adjusting the force applied to a microneedle from a drive source is disclosed. The microneedle give adjustment apparatus comprising an adjustment dial having a non-circular aperture through its center, a give slide comprising a drive end and an inner circumference, the inner circumference defining a substantially cylindrical cavity and having a threaded portion about the inner circumference of the cavity and the drive end having an opening into the cavity, a drive pin comprising a first pin end that is dimensioned to slidably pass through the opening of the give slide drive end and dimensioned to engage the aperture of the adjustment dial so that the first pin end rotatably engages the adjustment dial about the central axis and allows for the first pin end to linearly oscillate through the aperture co-axially with the central axis, a collar having a diameter larger than the opening of the drive end so that the collar, and thus the drive pin, is retained within the cavity and dimensioned to allow the drive pin to slide linearly within the cavity, and a second pin end, a give nut dimensioned to threadedly engage the threading of the give slide cavity and adapted to be rotatably engaged by the second pin end so that the second pin may linearly oscillate co-axially with the central axis, and a spring positioned between the give nut and the collar which imparts a separating force between the drive pin and the give nut.

In a further embodiment, a microneedle machine apparatus is disclosed, comprising a means for converting rotational motion of a motor driveshaft end into reciprocating oscillating motion of a microneedle or microneedle pack, such that the driveshaft end is substantially co-axial to the linear oscillating motion of the microneedle(s), a means for adjusting the impact force of the microneedle, a means for detachably coupling a disposable microneedle cartridge to the impact adjusting means, and a means for adjusting the length at which the microneedle(s) extends out from the tip of the microneedle cartridge as the microneedle(s) oscillates. Embodiments of the present disclosure may include components manufactured from various materials based upon the contemplated use. For embodiments that are contemplated for human use, materials that are durable, cleanable or autoclaveable, and sanitary are contemplated to be within the scope of the present invention. By way of example and not limitation, materials may be stainless steel, anodized aluminum, or polycarbonates.

The present disclosure may address one or more of the problems and deficiencies of the prior art discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

The following description and the annexed drawings set forth certain illustrative aspects of the disclosure. These aspects are indicative of only some of the various ways in which the principles of the disclosure may be employed, and the present disclosure is intended to include all such aspects and their equivalents. Other advantages and novel features of the disclosure will become apparent from the following description when considered in conjunction with the drawings.

BRIEF DESCRIPTION OF THE DRAWINGS

The disclosure can be readily understood by considering the following detailed description in conjunction with the accompanying drawings, in which:

FIG. 2A illustrates a lateral view of an embodiment of a microneedle machine in accordance with the disclosure comprising a rotary motor, housing, grip, and microneedle cartridge.

FIG. 2B illustrates a lateral view of FIG. 2A showing the grip and microneedle cartridge component and the housing having threading, an adjustment dial, and rotary motor.

FIG. 2C illustrates a lateral view of FIG. 2A showing separation between the microneedle cartridge, grip, give adjustment, motion translation device, ratchet disc, housing, and drive motor.

FIG. 3A illustrates a lateral view an embodiment of a microneedle machine in accordance with the disclosure comprising a grip and microneedle cartridge and the housing having threading, an adjustment dial, and rotary motor.

FIG. 3B illustrates a lateral crossectional view of FIG. 3A along section A-A, showing the grip with microneedle cartridge inserted thereto, together with threading and grooves, and the microneedle motion translation and impact adjustment, together with motor.

FIG. 5A illustrates a lateral view of an embodiment of a microneedle machine in accordance with the disclosure comprising a rotary motor, housing, grip, and microneedle cartridge.

FIG. 5B illustrates a partially exploded lateral view of FIG. 5A showing the grip and microneedle cartridge component and the housing having threading, an adjustment dial, and rotary motor.

FIG. 5C illustrates a lateral partially exploded view of FIG. 5A showing separation between the microneedle cartridge, grip, housing, ratchet disc, motion translation device, and drive motor.

FIG. 6A illustrates a lateral view an embodiment of a microneedle machine in accordance with the disclosure comprising a grip and microneedle cartridge and an adjustment dial, housing having threading and slot, and rotary motor.

FIG. 6B illustrates a lateral crossectional view of FIG. 6A along section B-B, showing the grip with microneedle cartridge inserted thereto, together with threading and grooves, and the microneedle motion translation and impact adjustment, together with motor.

DETAILED DESCRIPTION

Figure 1:
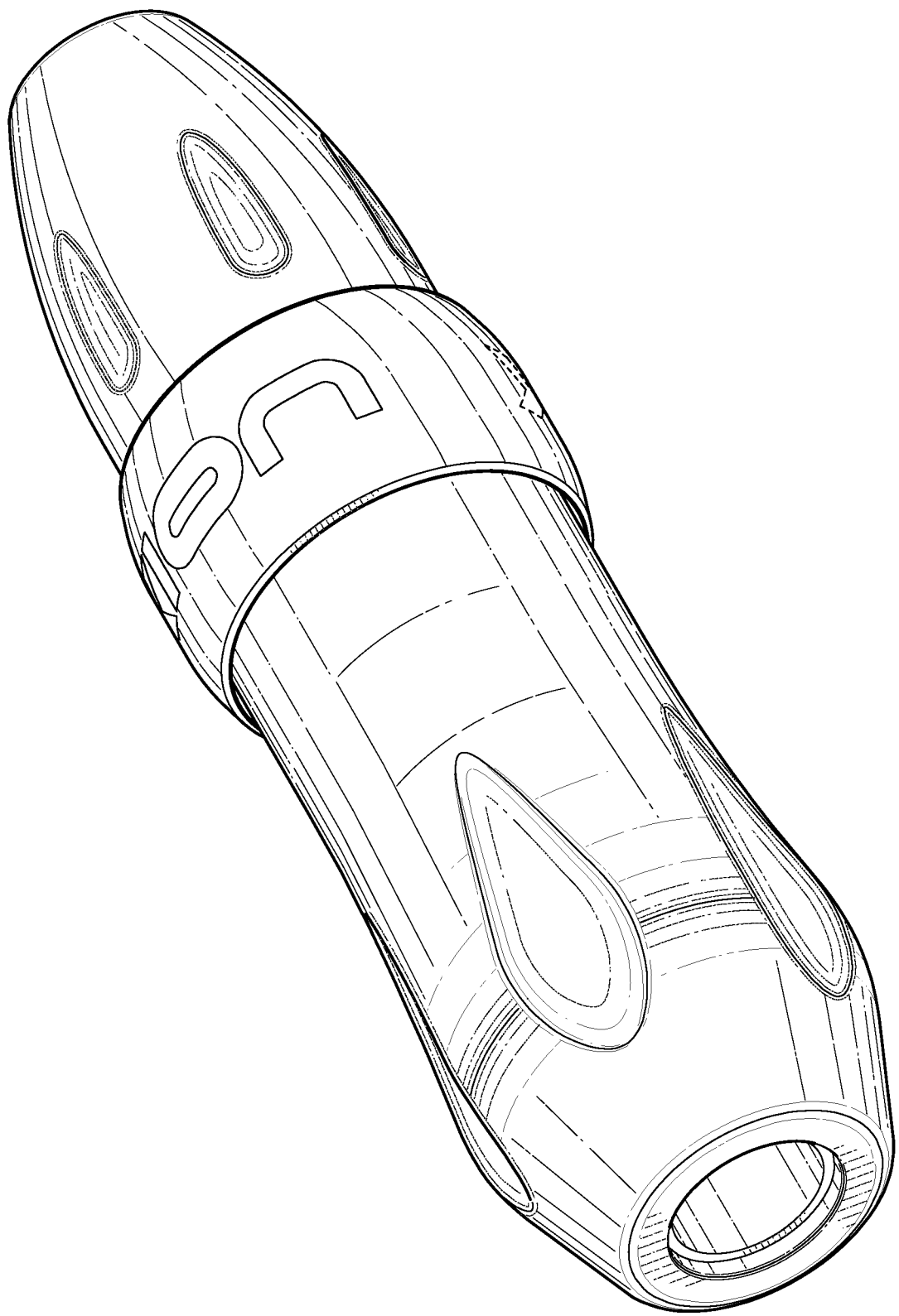
FIG. 1 illustrates a perspective view of an embodiment of a microneedle machine in accordance with the disclosure comprising a rotary motor, housing, and grip having an end to accept a microneedle cartridge.

The following detailed description and the appended drawings describe and illustrate various embodiments of the disclosure solely for the purpose of enabling one of ordinary skill in the relevant art to make and use the disclosure. As such, the detailed description and illustration of these embodiments are purely exemplary in nature and are in no way intended to limit the scope of the disclosure, or its protection, in any manner. It should also be understood that the drawings are not to scale and in certain instances details have been omitted, which are not necessary for an understanding of the present disclosure, such as conventional details of fabrication and assembly.

In the Summary above, in the Description, and in the accompanying drawings, reference is made to particular features of the disclosure. It is to be understood that the disclosure in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the disclosure, and in the disclosure generally.

The term "comprises" and grammatical equivalents thereof are used herein to mean that other components, structures, steps, etc. are optionally present. For example, an article "comprising" (or "which comprises") components A, B, and C can consist of (i.e., contain only) components A, B, and C, or van contain not only components A, B, and C, but also one or more other components or structures.

The term "at least" followed by a number is used herein to denote the start of a range beginning with that number (which may be a range having an upper limit or no upper limit, depending on the variable being defined). For example, "at least 1" means 1 more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

The term "mechanical features" is used herein to mean features of a component, mechanical or geometric, which have a functional purpose of attaching or linking that component to one or more other components with compatible or corresponding mechanical features. An example of a mechanical feature is a slot in a component, where said slot is designed to accept a tab from another component and the union of the slot and tab from the two components effectively links, attaches, fixes, and/or locks the components together. The term "mechanical features" refers to, but is not limited to: hooks, hook and loop fasteners, slot and tabs, all male and female fasteners, screws, bolts, nuts, holes that have been tapped, latches, pins, etc.

While the specification will conclude with claims defining the features of embodiments of the disclosure that are regarded as novel, it is believed that the disclosure will be better understood from a consideration of the following description in conjunction with the figures, in which like reference numerals are carried forward.

The components of the apparatus are configured to accept a multiple types of needle cartridges. The components are arranged in a linear fashion, aligned to a common central axis, so that the motor assembly is attached to the drive mechanism such that the main shaft of the motor is mechanically coupled to coupling features in the drive mechanism or coupled directly to the give adjustment mechanism. The drive mechanism, mechanically coupled to the motor, converts the rotational motion of the motor shaft into a reciprocating rectilinear motion. The grip portion is configured to accept various typed of needle cartridges. The grip portion is further configured to mechanically couple to the drive mechanism. When assembled to the drive mechanism, the grip portion is coaxially aligned to the drive mechanism and the motor assembly. In this configuration, the rotational motion of the motor is translated into a reciprocating rectilinear motion by the drive mechanism, which is then mechanically imparted to the needle cartridge constrained in the grip portion, thereby causing the needle to reciprocate co-axially to the central axis. A give adjustment mechanism may be placed between the motion translation mechanism and needle cartridge, or may be driven by a linear oscillating motor. Since the various components of the apparatus all assemble along a common central axis, the final apparatus is configured in a radially symmetric format that affords an operator a much more comfortable and familiar tool for doing their work.

Certain embodiments of the present disclosure may be used for, but are not limited to, the etching of skin, tattooing, micropigmentation, therapeutic microneedling, scarification, and other therapy or body modification. It is contemplated, however, that the use of certain embodiments of the present invention in other applications beyond traditional tattoo use, is within the scope of the present invention. For example, the invention may be used for cosmetic tattooing, use in applications other than on humans, or for other artistic, medical, or industrial uses.

In one embodiment, a microneedle drive apparatus for converting rotational motion into reciprocating approximately linear motion is disclosed. The microneedle drive apparatus comprising a housing having substantially radial symmetry about a central axis, a rotary motor having an output driveshaft end which is insertable into the housing and rotates substantially co-axially to the central axis, and a motion translation device. The motion translation device is dimensioned to fit within the contoured barrel housing and comprises an offset connectable to the driveshaft end such that the driveshaft rotatably drives the offset a distance from the central axis, a follower adapted to slide linearly in a plane substantially orthogonal to the central axis and having a groove dimensioned to be engaged by the offset, and a bellcrank having a fulcrum about which the bellcrank pivots, and first arm and a second arm. The first bellcrank arm is adapted to be driven by the follower so that as the follower slides within the housing, the bellcrank pivots at the fulcrum so that the second arm oscillates approximately linearly and approximately parallel to the central axis.

The housing of a microneedle drive apparatus of the disclosure may include a cartridge end, which is dimensioned to accept a microneedle cartridge so that the second arm of a bellcrank of the motion translation device engages the microneedle cartridge such that the second arm of the bellcrank reciprocally drives the microneedle within the microneedle cartridge.

A further optional embodiment of the disclosure may include a grip that has substantially radial symmetry about the central axis and which threadingly engages the housing through a corresponding threads. The end of the grip may include an opening to accept a microneedle cartridge at an end distal to the housing mating portion. The grip may have substantially radial symmetry about the same central axis as the housing, so that the grip translates onto the housing as the grip is rotated about that central axis relative to the housing, and which thus changes the oscillatory displacement of the microneedle.

The disclosure may also optionally include a bearing as the pin attached to the driveshaft end, as well as a counterweight of such shape and mass so as to reduce vibration produced by the offset bearing as it orbits around the central axis.

In yet another embodiment of the disclosure, the yoke of a microneedle drive apparatus may include a plurality of slide facets that reduce the surface area contact between the yoke and the housing so that friction between the yoke and the housing is reduced as the yoke slidingly oscillates within the housing.

An optional embodiment of a drive apparatus includes a spring between the motion translation device and the housing such that the motion translation device returns to a retracted position. The retracted position ensures that the pointed end of a microneedle does not extend outward from a microneedle cartridge tip when the machine is not in use, and facilitates higher oscillation frequencies than the return force applied by the microneedle cartridge alone.

The disclosure may include a ratchet disc having a slot and at least one positive detent. The ratchet disc is configured to slottedly mate with the housing while the housing mating portion of the grip may have at least one groove parallel to the central axis so that it engages with the detent or detents on the ratchet disc so that when the grip is rotated about the central axis relative to the housing, the ratchet disc when mated to the corresponding slot in the housing operatively interacts with the groove or grooves in the grip.

In yet another embodiment, a microneedle give adjustment apparatus for adjusting the force applied to a microneedle from a drive source is disclosed. The microneedle give adjustment apparatus may comprise an adjustment dial having a non-circular aperture through its center and a give slide comprising a drive end and an inner circumference. The inner circumference of the give slide may define a substantially cylindrical cavity within the give slide which may also have a threaded portion about the inner circumference of the cavity. The drive end may have an opening into the cavity. A drive pin may also be included that has a first pin end and a second pin end, and a collar between the first end and the second end. The first pin end may be dimensioned to slide through the opening of the drive end while also engaging the aperture of the adjustment dial so that the first pin end rotatably engages the adjustment dial without rotating the give slide, but such that the first pin end may slide through the give slide opening to permit the pin to linearly oscillate through the aperture co-axially with the central axis. The collar may be dimensioned to have a diameter larger than the opening of the drive end so that the collar, and thus the drive pin, is retained within the cavity while also allowing the drive pin to slide rectilinearly within the cavity. The second pin end is dimensioned to engage a give nut, while the give nut is dimensioned to threadedly engage the threading of the give slide cavity so that the second pin end rotatably engages the give nut while also allowing the second pin end to linearly oscillate co-axially with the central axis through the opening in the give nut. A spring may be positioned between the give nut and the collar so that force is applied to between the drive pin and the give nut.

The disclosure may include microneedle give adjustment apparatus where the give slide may have one or more facets along its sides that reduce the surface area point of contact between the give slide and the housing. The facets may reduce friction as the give slide slidingly reciprocates within the housing.

In a further embodiment, a microneedle machine apparatus is disclosed, comprising a means for converting rotational motion of a motor driveshaft end into reciprocating oscillating motion of a microneedle or microneedle pack, where the driveshaft end is substantially co-axial to the linear oscillating motion of the microneedle(s), together with a means for adjusting the impact force of the microneedle, a means for detachably coupling a disposable microneedle cartridge to the impact adjusting means, and a means for adjusting the length at which the microneedle(s) extends out from the tip of the microneedle cartridge as the microneedle(s) oscillates. As referenced in this disclosure and claims, "a microneedle" is not to be construed as a structural limitation, but is instead descriptive of the functional result of the disclosed structure. Microneedling describes a rectilinear motion wherein the needle is rapidly inserted and withdrawn from the skin of a person or animal.

The needle unit, also called a needle cartridge, may include one or more needles contained within the unit. Needles may be hollow or non-hollow, depending on the application. By way of example and not limitation, a hollow needle may be used to apply permanent makeup to a patient's skin, relying on the capillary action within the hollow of the needle to take up and subsequently deposit medical grade skin colorant. By way of another example and not limitation, a non-hollow, or solid, needle may be utilized to stimulate a patient's skin with micropunctures and thus promote certain biological responses within the patient's body. These processes may be cosmetically restorative by promoting a natural healing process. Other types of implements may be provided within a cartridge other than needles. A pin with blunted tip, micro-scoop, knife or flat blades, needle or pin with a hooked end, or other configuration of a metallic or sterilizable rigid material to achieve the desired goals of a reciprocating pen style machine.

The diameter and aperture of the needle and frequency of reciprocation of the machine may be configured to accept and deposit into a patient live cells, such as stem cells. Small molecules or liquids encapsulated in a liposome may also be delivered into a patient's skin through a reciprocating pen style machine.

With regard to the housing or grip of the reciprocating pen style machine, its geometric symmetry need not be perfect or absolute. An objective of the disclosure is that the device can be rotated in a user's hand to change the tip orientation without significantly affecting the feel or without significantly affecting the utility of the device. Thus, non-symmetric features that do not substantially affect or interfere with the goals of reciprocating pen style machine are contemplated by the disclosure. Features which may make the housing imperfectly radially symmetric may include ornamental or decorative features, variations in detents to accommodate different grip styles, and so on. The grip may be configured with gripping means. Such gripping means may be recesses, grooves, knurls, or other known surface features or treatments that allow the user to securely grip the apparatus.

It is a further objective of a pen style machine to fit within a user's hand. Hand sizes vary among users, and it is contemplated by the disclosure that the housing or grip of the device may be varied to accommodate different size hands, with or without changing the size or scale of the machine's internal components. Similarly, individual tastes and preferences as to size of the machine impact a user's comfort. Accordingly, the housing or grip portion of the device may range in diameter from about 7 millimeters up to about 45 millimeters.

Weight distribution in the pen style machine is a further desirable feature that enhances user comfort and increases precision use of the device. Materials used in certain components may be selected to achieve optimal weight distribution in the machine, end-to-end as between the needle end and the motor end, such that the machine feels balanced while in a user's hand. Similarly, materials may be selected to optimize axial weight distribution. By way of example and not limitation, denser materials may be selected for the grip component of the machine to counter-balance the weight of the motor, battery, or other components opposite from the needle-end of the device so as to achieve an optimal center of gravity or center of mass.

A further objective of a pen style machine is to reduce heat and vibration, thus decreasing user fatigue and increasing user comfort. A pen style machine may include a counterbalance to an offset bearing. The mass of the counterbalance may be adjusted according to the distance which the offset bearing is from the motor's driveshaft to reduce or eliminate vibration otherwise produced by an unbalanced rotating mass.

The driveshaft powering the pen style machine may be rigid or flexible. By way of example and not limitation, the motor may be located outside the housing, enclosed in a separate unit, and connected to the pen style machine through a long flexible driveshaft. Separating the motor from the rest of the machine isolates noise and vibration produced by the motor. The end of the flexible driveshaft may have a connecting mechanism designed to mate with the pen housing or grip, such that the driveshaft end can be reversibly connected to the housing or grip. As the driveshaft connects with the pen housing, the driveshaft end should share the common axis of the housing. The driveshaft end may also have an offset and a counterweight, which may be detachably coupled to the driveshaft.

Power supplied to the motor may be provided by traditional direct current through an RCA connection, but other embodiments are also contemplated. By way of example and not limitation, a motor not contained within the pen housing or grip may be connected to conventional power outlets providing 110V or 220V alternating current. In other embodiments, the motor may be powered through a battery contained within the pen housing or grip. Such battery-based power supply may be detachable or hot swappable within the machine, allowing a user to quickly remove a drained battery and replace it with a fully charged battery for continuous, cord free use of the machine. A pen style machine having no power cord or other wired connections increases the freedom of movement of the device by the user, reduces tangling and cord management, and increases cleanliness by having a completely self-contained machine.

The motor may have a positional memory of the rotor relative to the stator such that the motor, when not operated, has a resting position. Such a resting position obviates the need for a spring to ensure withdrawal of the needle into a retracted and safe position when the apparatus is not being operated. The positional memory may be achieved by magnetic design or solenoid within the motor, or through signals from the power supply to the motor. Similarly, the motor may have a positional memory where the needle remains stationary in a fully extended position, allowing the operator to inspect the condition of the needle.

An offset may be attached to the driveshaft end such that the rotational motion drives the offset about the central axis of the driveshaft. The offset is configured to matingly engage a follower in the nature of a Scotch yoke or crank and slider. The follower is constrained within a housing, and is configured to slide back and forth within the housing in a plane parallel to the plane of rotation of the offset. The follower has a groove on its face, the width of the groove being dimensioned to accept the offset, and the length dimensioned to the diameter of rotation of the offset. The offset engages the groove, causing the follower to slide in one direction while the offset slides within the groove in the orthogonal direction. In this way, rotational motion of the driveshaft is translated into linear oscillating motion of the follower. The offset may vary in distance from the center of the driveshaft end. Changing the diameter of rotation of the offset about the driveshaft end produces a change in the needle stroke as a consequence of the Scotch yoke motion translation device. The present disclosure contemplates the apparatus may be packaged as a kit, and include multiple interchangeable offsets that produce varying diameter of rotation, and thus varying needles stroke.

The area of contact between the follower and the housing or other constraining components may have certain features to reduce the total surface area of contact between them, such as small planar surfaces or facets which keep the follower operably constrained within the device while reducing the sliding friction between the follower and the housing, retaining ring, or other components as the follower slidingly oscillates.

By way of example and not limitation, in one embodiment, the follower may have an approximate linear displacement of about 5.5 millimeters as it slides within the housing.

The opposite face of the follower is configured to engage a rocker arm or bellcrank. The fulcrum of the bellcrank is fixedly constrained within the housing. The fulcrum may have a pin one or more bearings, or a combination of a pin and bearings to allow the bellcrank to rotatably oscillate about the fulcrum as it is driven by the follower. The follower may have a groove to accommodate a pin on one arm of the bellcrank. The groove may be dimensioned to allow the pin to rotate as the follower slides, thus pushing the bellcrank. The bellcrank may be dimensioned to change the amount of displacement imparted on the give slide or needle cartridge. The rocker arm ratio of the bellcrank may be 1:1, although other ratios are contemplated to achieve sufficient displacement, torque, and oscillation of the end of the second arm. The bellcrank's angle may be approximately ninety degrees, but other angles are contemplated to achieve an approximately linear oscillation of the end of the second arm. The arcing motion produced at the end of the second arm need not be perfectly linear or even substantially linear, but rather the sagitta should be sufficiently small to allow the second arm to depress a needle cartridge through the arm's full range of motion, either directly or indirectly through an intermediate tappet or other component, such as the give adjustment device disclosed herein.

Other configurations of the motor, offset, follower, and bellcrank are contemplated to provide more or less displacement of the needle and variations in size of the components. By way of example and not limitation, a motor with higher torque, together with follower having smaller displacement combined with a bellcrank providing a 2:1 motion translation ratio may result in an overall narrower device while achieving substantially the same desired mechanical output at the needle tip.

A give adjustment mechanism is also disclosed. A person's skin can vary widely on a single individual depending on the area being worked upon, and can also vary from person to person. Some skin is very soft and thus more easily pierced by a needle, while other skin can be comparatively resilient and may require more force to drive the needle through the upper layers of epidermis to the required depth to deposit micro pigments or to achieve therapeutically beneficial stimulation.

A user may rotate the give knob which thus increases or decreases the compression of the give spring, and thus changes the "give" of the needle. The give may range from relatively low needle impact force ("soft") to relatively high needle impact force ("hard"). In the soft setting with the spring in a state of low compression, the drive pin is allowed to slide within, or partially retract into, the give slide. In the hardest setting, the spring is completely compressed, allowing no movement between the drive pin and the give nut and thus the entirety of the force applied by the bellcrank to the give slide is directly translated to the drive pin without absorption by the spring. In varying settings between complete compression and low compression, the give spring can absorb some of the needle impact force encountered as the needle hits a work surface. For example, some areas of skin are relatively thin with bony structures lying just beneath the body's surface. In other areas, fatty deposits below the skin surface may require a harder needle impact to ensure proper needle penetration into the skin. In this way, various areas of a person's body may require a range of needle impact forces to achieve proper needle penetration to the proper depth in a person's skin.

The give adjustment mechanism may be driven by a rotational motion translation device like that disclosed herein, or it may be driven by a linear oscillating motor without the need for a motion translation mechanism.

The drive pin, in operative response to the give spring within the give slide, may retract into the give slide with a displacement of between about 1.6 millimeters to zero millimeters. The greater the displacement, the softer the impact. A zero displacement would yield a hard impact, while a displacement of 1.6 millimeters would produce a soft impact.

The area of contact between the give slide and the give housing or other constraining component may have certain features to reduce the total surface area of contact between them, such as scalloping or grooves which reduce sliding friction while keeping the give slide operably constrained within the device as the give slide slidingly oscillates.

The interior of the grip may have an internally threaded portion. These threads are configured to accept the externally threaded portion of the housing. This threaded engagement allows for the needle depth to be adjusted. To shorten the needle depth, a user rotates the grip relative to the housing in one direction. In order to lengthen the needle depth, the user may turn the grip (relative to the housing) in the opposite direction. This rotation of the grip relative to the housing changes the distance between the grip-cartridge combination and the housing. In this way, the needle depth may be adjusted from zero up to approximately four millimeters.

The pen style machine may optionally include a means for identifying the range of the needle throw, such as having numbers or other markings on the housing with a corresponding constrained viewing area which indicates needle throw based on the relative spacing between the grip and the housing.

Methods of using a pen style machine are also contemplated by the disclosure. In one embodiment, a method of stimulating an innate healing response of a person's skin is disclosed, comprising the steps of providing a substantially radially symmetric microneedling machine, providing a patient, identifying a target area of skin to be stimulated on the person's body, and operating the microneedling machine to stimulate the patient's skin for a period of time sufficient to impart a therapeutic effect. In another embodiment, a method of introducing an inert substance into the skin of a person or animal comprising the steps of providing a substantially radially symmetric microneedling machine, providing a substance capable of being accepted into an aperture of a hollow microneedle, identifying a target area of skin into which the substance will be implanted, introducing the substance into the microneedle, and operating the microneedling machine on the skin to implant the substance to the desired depth. A cellular therapy, biologic therapy, small molecule drug, vaccine, or other medically therapeutic substance may also be introduced into a patient's skin to produce a therapeutic result.

Referring now to the figures in general, and to FIG. 1 in particular, an embodiment of the present disclosure in the form of a pen style tattoo machine apparatus is disclosed showing a perspective view of the device without microneedle cartridge. The apparatus demonstrates an approximate radial symmetry about a single central axis. In FIG. 2, a pen style microneedle machine is disclosed, the apparatus comprises the following components and structures: a motor assembly 150, a drive mechanism 160, and a grip 170. The components are related as follows: the motor assembly 150 is mechanically coupled to a first end of the drive mechanism 160, and the grip 170 is mechanically coupled to a second end of the drive mechanism. A microneedle cartridge 140 is mechanically coupled to the grip 170.

FIGS. 2 and 3 show one embodiment of a pen style microneedling apparatus 100 together with needle cartridge 140. The grip 170 is a contoured barrel configured to accept a needle cartridge at one end (needle cartridge is shown for reference in some figures) and the drive mechanism 160 at the other, distal, end. A motor drive assembly 150 mates with the drive mechanism. Mechanical features, such as threaded surfaces, are integral to the interior portion of the grip and are configured to engage with mating threaded surfaces on the drive mechanism such that a rotation of the grip will translate it further onto the drive mechanism, and an opposite rotation will translate it further away from the drive mechanism. In this way, the drive pin distance from the corresponding pin on a needle cartridge can be adjusted, and thus the stroke of the needle in the needle cartridge is adjusted to produce greater or lesser extension outward from within the cartridge. Embodiments of the invention contemplate additional detent features engaging between the drive mechanism and the grip such that a user may rotate the grip to a desired position and the detent features will hold the grip in place. In this way the user may select a desired stroke depth, as discussed above.

FIG. 3B shows motor assembly 150 comprised of a motor housing 151, a motor 153, and an electrical connector 155. The motor 153 is a direct current (DC) powered motor with a drive shaft on one end and electrical lead connections on the other end. The electrical connector 155 is a two-conductor connector that is electrically coupled to the electrical lead connections of the motor 153. In a preferred embodiment of the apparatus, the electrical connector 155 is a female RCA type connector, although other embodiments may include clip, plug, or other electrical connections capable of delivering a direct current to the motor. The motor 153 and the electrical connector 155 are constrained in relation to each other by the motor housing 151. The motor housing 151 may be of any rigid and cleanable material. A preferred embodiment of the motor housing 151 is CNC-machined aluminum that has been treated with a durable and cleanable surface finish. The motor housing is substantially cylindrical and hollow such that the motor and electrical connector may be fixedly attached inside. One end of the motor housing may taper down to allow the electrical connector to mount and protrude past the edge of the motor housing, or the electrical connecter 155 may be recessed within a portion of the motor housing 151 so as to protect the electrical connector. A second end, opposite the first end, opens to accept the motor. The motor is fixedly attached within the motor housing such that the drive shaft of the motor protrudes past the motor housing second end. A drive gear is fixedly attached to the end of the drive shaft 156 such that the gear rotates together with the drive shaft rotation. The motor housing is configured such that the motor housing, the motor, and the electrical connector, when all assembled, share a common central axis 158. The motor housing further comprises locking features 157, such as slots, tabs, or threading, which are configured to enable the motor assembly 150 to mechanically couple with mating features in the drive mechanism 160 thereby allowing both components to remain in operational relation to each other. A grip may be configured to threadingly engage the drive mechanism such that rotation of the grip relative to the drive mechanism adjusts the stroke of the needle.

The drive mechanism converts the rotational motion of the motor into an axial reciprocating motion. FIG. 3B shows a drive mechanism according to an embodiment of the present invention.

Figure 4:
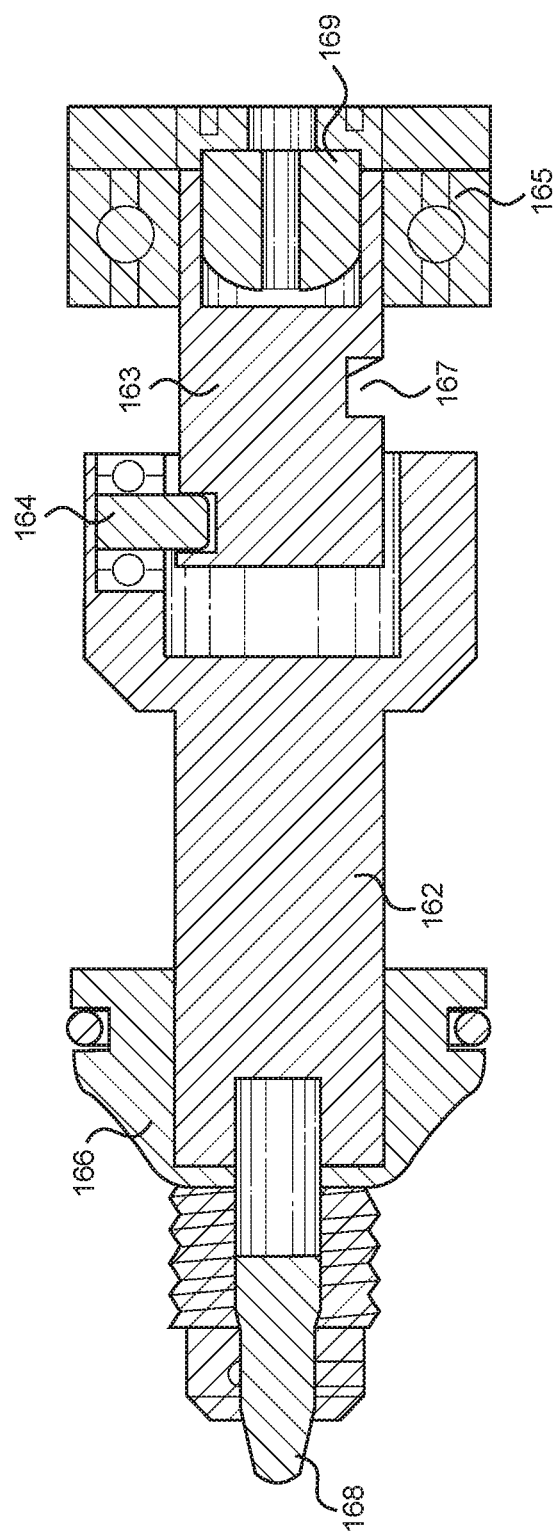
FIG. 4 illustrates an embodiment of a combined microneedle drive and give adjustment apparatus.

FIG. 4 shows the drive mechanism 160 comprised of a housing (not shown) encasing a slider 162, a drive barrel 163, a barrel pin and bearing 164, a barrel bearing 165, a give cap 166, helical groove 167, and a drive pin 168. The drive barrel 163 is rotationally coupled to the barrel bearing 165 and configured to accept the drive gear 169 such that rotation of the gear by the motor directly rotates the drive barrel. The body of the drive barrel is further comprised of a helical groove 167 about its outer circumference. The position of the barrel pin and bearing are linearly fixed in relation to the housing 161. The barrel pin 164 is integral to the slider 162, fixed in location, and is configured to be slidingly communicative with the helical groove 167 in the drive barrel. As the drive barrel 163 rotates, the barrel pin 164 travels along the groove 166, which, in turn, translates the slider 162 back and forth with respect to the drive barrel. In this way, the rotational motion of the motor is converted into a reciprocating linear motion of the slider orthogonal to the rotation of the motor.

The end of the slider opposite the drive barrel may further comprise a drive pin 168. In a preferred embodiment of the apparatus, the drive pin is a metal rod partially inserted and fixedly attached to the slider. The drive pin makes mechanical contact with a needle cartridge and pushes the needle back and forth. This drive pin may, in further embodiments, be spring loaded such that the drive pin may have selective "give" as it pushed against the needle cartridge. This selective give is adjusted by rotating the grip 170, the give adjustment knob 166, or another knob or wheel within the grip. As the grip 170 or knob or wheel is rotated, it interacts with threads on the drive mechanism housing and is resisted in the opposite direction by the give cap 166. The interaction of these components allows the user to "dial-in" a desired needle impact force or give by merely rotating the grip portion clockwise or counter-clockwise relative to the drive mechanism. In this way, an embodiment of the apparatus can be configured to have both a give adjustment and a stroke adjustment.

Referring to FIG. 5, another embodiment of the present disclosure in the form of a pen style microneedle machine apparatus 101 is disclosed. The apparatus comprises the following components and structures: a motor assembly 300, a motion translation mechanism 500, a give adjustment mechanism 200, and a grip 400. The components are related as follows: the motor assembly 300 is mechanically coupled to a first end of the motion translation mechanism 500, which is housed within the give adjustment mechanism 200, and the grip 400 is mechanically coupled to a second end of the give adjustment mechanism, and the two components are sealed by two O-rings on the outer circumference of the give adjustment mechanism. A microneedle cartridge 140 is reversibly coupled to the grip 400.

FIG. 6, shows a preferred embodiment of pen style microneedle machine apparatus with motor assembly, motion translation mechanism, give adjustment mechanism, and needle depth adjustment, together with a microneedle cartridge.

The motor assembly 300 is comprised of a motor housing 301, a motor 310, an electrical connector 390, and O-ring 340. The motor 310 is a direct current (DC) powered motor with a drive shaft on one end and electrical lead connections on the other end. The electrical connector 390 is a two-conductor connector that is electrically coupled to the electrical lead connections of the motor 310. In a preferred embodiment of the apparatus, the electrical connector 390 is a female RCA type connector. The motor 310 and the electrical connector 390 are constrained in relation to each other by the motor housing 301. The motor housing 301 may be of any rigid and cleanable material. A preferred embodiment of the motor housing 301 is CNC-machined aluminum that has been treated with a durable and cleanable surface finish. The motor housing is substantially cylindrical and hollow such that the motor and electrical connector may be fixedly attached inside. One end of the motor housing may taper down to allow the electrical connector to mount in a recess within a portion of the motor housing so as to protect the electrical connector. A second end of the motor housing, opposite the first end, opens to accept the motor. The motor is fixedly attached to the motor housing such that the drive shaft of the motor protrudes past the motor housing second end. An O-ring 340 sits within a circumferential groove on the motor housing 301 and is positioned such that when the motor housing engages the give housing 201, a seal is formed. The motor housing is configured such that the motor housing, the motor, and the electrical connector, when all assembled, share a common central axis.

The motion translation mechanism 500 is comprised of a combination offset pin and counterweight 320, an offset pin bearing 330, a follower 520 and a bellcrank 510, where the drive mechanism translates the rotational motion of the motor driveshaft to rocking reciprocating motion at the second arm of the bellcrank. The combination offset pin and counterweight 320 is fixedly attached to the driveshaft end such that the offset pin, counterweight, and offset pin bearing are rotatably driven by the driveshaft end. The follower 520 is operably constrained in relation to the motor assembly by the give housing 201 and a retaining ring 550. The follower has a groove on the motor-facing side configured to accept the offset bearing 330 such that rotation of the offset bearing linearly slides the follower while the offset bearing travels linearly within the groove and orthogonal to the direction of the follower sliding motion. On the opposite side of the follower 520 is a second groove configured to mechanically engage with the first arm of the bellcrank 510. The bellcrank is mechanically constrained at its fulcrum within the give housing 201. The second arm of the bellcrank rockingly drives the give adjustment mechanism 200.

The give adjustment mechanism 200 is comprised of a give slide 210, a give nut 240, a drive pin 220, a give knob or adjustment dial 250, and a retraction spring 290. The give slide 210 contains a hollow inner portion which slidably constrains the drive pin 220 and threadingly engages the give nut 240. The give slide 210 has an opening at its pin end through which a portion of the drive pin protrudes. The drive pin 220 has a first end, a middle collar, and a second end. The drive pin is slidably constrained within the give slide 210 by the middle collar having a diameter larger than the first pin end. The first pin end is a hexagonal prism that rotatably engages the give knob 250 through a corresponding hexagonal opening in the center of the give knob, and through which the first pin end may slide. The give knob is reversibly constrained to the give housing by a deformable O-ring. The second pin end is an oval prism that rotatably engages the give nut 240 through a corresponding oval opening in the center of the give nut, and through which the second pin end may slide. A spring integral to the give slide applies force between the drive pin collar and the give nut such that as the give nut's position within the give slide changes, the spring becomes more or less compressed between the give nut and the drive pin. The give knob 250 rotates the drive pin 220, which rotatably engages the give nut 240 along the threading on the interior of the give slide 210. The give slide is slidably constrained within the give housing 201 with a retraction spring 290 positioned between the give housing 201 and the give slide 210. When the give slide is not positively driven by the bellcrank second arm, the give slide assembly remains in a retracted position through the force of the spring. The spring also provides continuous physical communication between the give slide and the bellcrank second arm while the give slide is being driven by the bellcrank second arm to produce the desired linear reciprocating motion. Embodiments of the invention contemplate additional detent features engaging between the give housing and the give knob such that a user may rotate the give knob to a desired position and the detent features will hold the give knob in place. In this way the user may select a desired needle "give", as discussed above.

The needle stroke adjustment mechanism is comprised of threading 420 inside the grip, corresponding threading 204 on the exterior of the give housing, grooves 410, and a ratchet disc (not shown). The give housing 201 has a first end and a second end. The first end opens to engage the motor housing 301, and the second end is configured to mate with a grip 400. Threading 204 on the give housing corresponds to threading 420 on the grip such that when assembled, the grip 400 and give housing 201 can be rotated relative to each other and thus adjust the relative distance between the grip and the give housing. Changing the distance between the grip and the give housing changes the "stroke" or length which the needle extends out from the cartridge 140 when the apparatus is operated. The interior of the grip 400 has a plurality of grooves 410 distributed radially about the interior of the grip of a length which is slightly greater than the total change in depth of the needle, so as to allow the ratchet disc (not shown) to continually engage the grooves at all stroke settings between the minimum and maximum extension. The cross-section of each of the grooves is configured to accept a detent portion on the ratchet disc. In this way, as the user rotates the grip and give housing to increase or decrease the needle stroke, the engagement between the grooved portion 410 and the detent portion on the ratchet disc creates mechanical stops that counteract inadvertent rotation, but allow intentional rotation upon application of sufficient torque to overcome the detent force. The give housing, grip, and motor housing may be of any rigid and cleanable material and are substantially cylindrical and are configured such that the give housing, motor housing, and grip, when assembled, share a common central axis.

The exterior of the grip 400 may be configured with gripping means. Such gripping means may be recesses, scalloping, grooves, knurls, or other surface features or treatments known in the art that allow a user to securely grip the apparatus.

Figure 7:
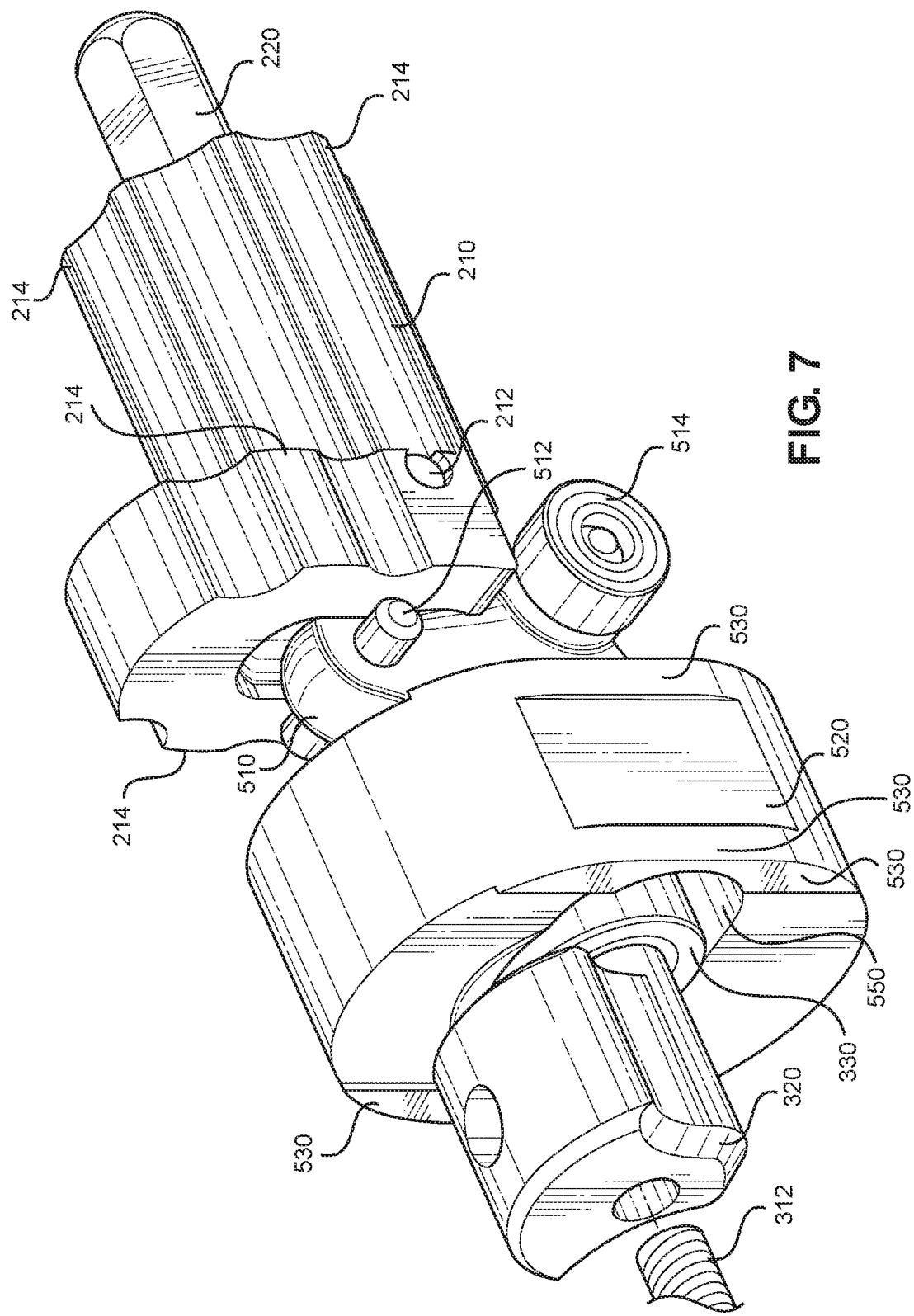
FIG. 7 illustrates a perspective view of an embodiment of a microneedle motion translation device and microneedle impact adjustment device.
Figure 8:
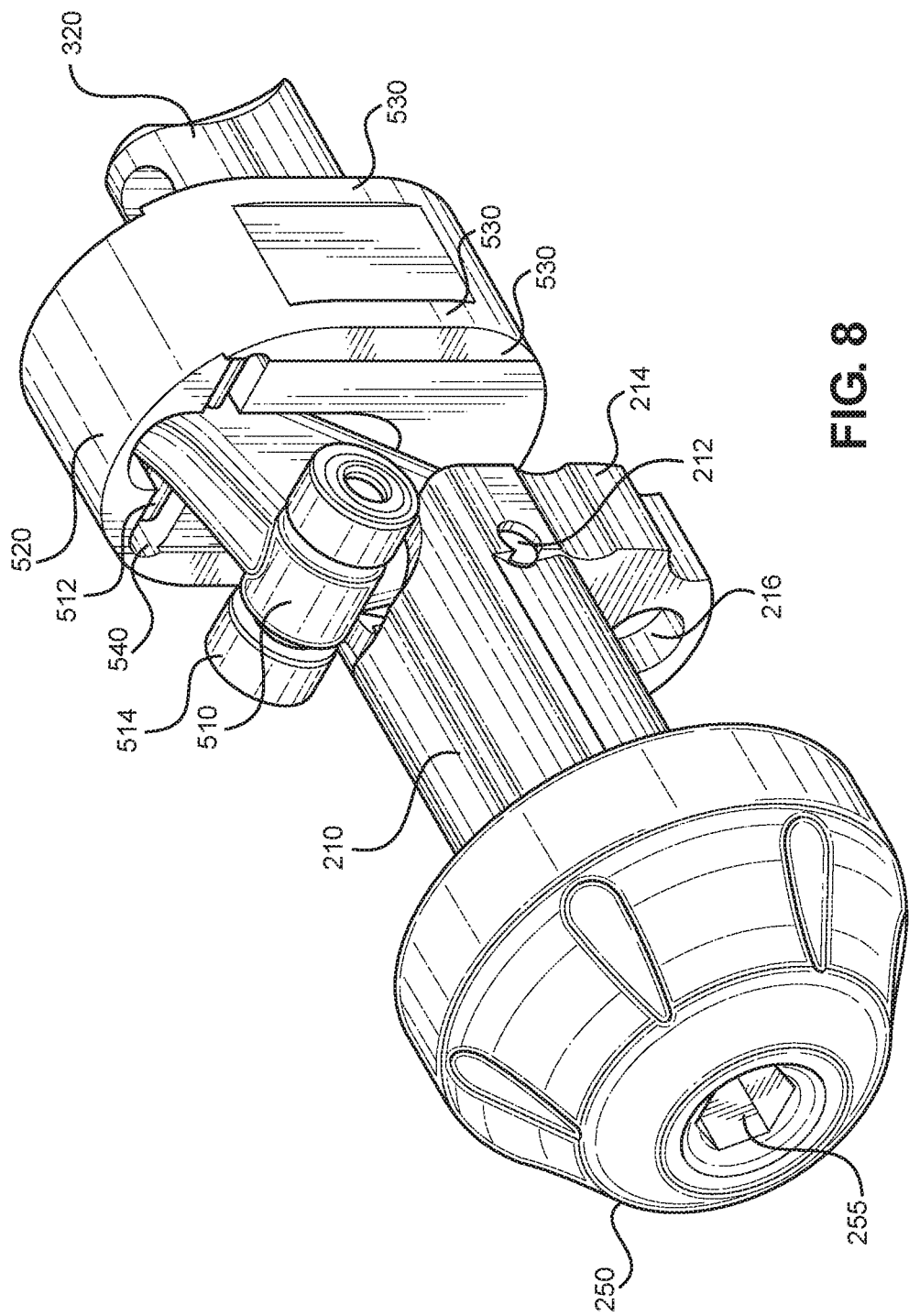
FIG. 8 illustrates a perspective view of an embodiment of a microneedle motion translation device and microneedle impact adjustment device.

FIGS. 7 and 8 show a preferred embodiment of a portion of the drive mechanism in relation to a portion of the give adjustment. The driveshaft end 312 reversibly couples with a combined offset pin counterbalance 320. The offset bearing 330 slidingly engages a follower 520 through an offset bearing groove 550 on the first side of the follower. As the driveshaft end 312 rotates, the offset bearing 330 orbits about the central axis and simultaneously oscillates in the groove 550 and slidingly drives the follower 520 in a linear direction orthogonal to the groove. The follower has facets 530 which reduce the surface area of contact between the follower and the give housing (not shown) and retaining ring (not shown). On the second side of the follower is a bellcrank groove 540 which accepts a bellcrank arm pin 512. The bellcrank 510 is fixedly constrained at a fulcrum within the give housing (not shown) and pivotably oscillates about a fulcrum pin and bearings 514. As the follower slides, it engages the bellcrank first arm, and the bellcrank rockingly engages a give slide 210 through a bellcrank arm pin 512. The give slide has a plurality of linear facets 214 which slidingly engage the give housing (not shown). The give slide may have a pin 212 to retain a give nut (not shown) within the give slide and prevent mechanical interference between the give nut and the bellcrank. A drive pin 220 extends outward from the give slide 210. As the give slide is slidingly driven by the bellcrank, the drive pin engages a needle cartridge (not shown). The drive pin rotatably engages a give knob 250 through an aperture 255. The give slide has a spring cup 216 to accept one end of a spring (not shown).

Figure 9A:
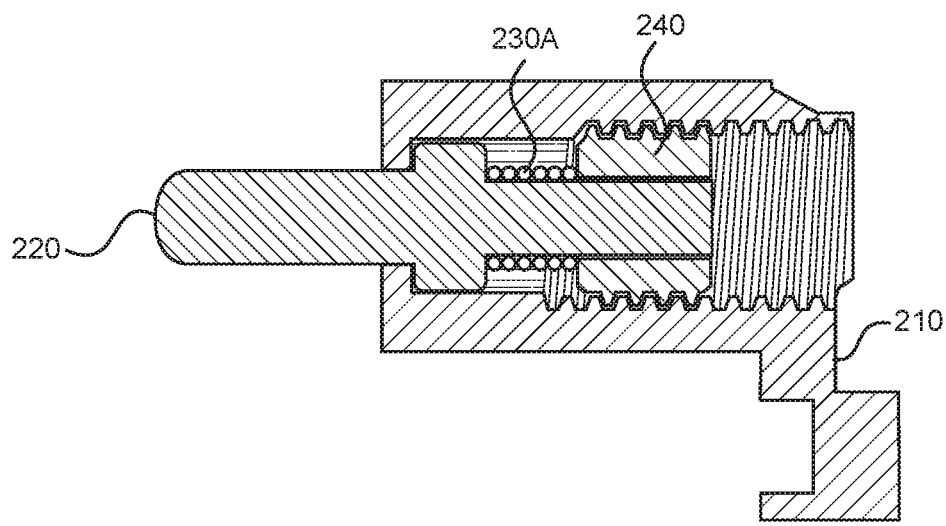
FIG. 9A illustrates a lateral crossectional view of an embodiment of a microneedle impact adjustment device wherein the adjustment nut is in a fully compressed position.
Figure 9B:
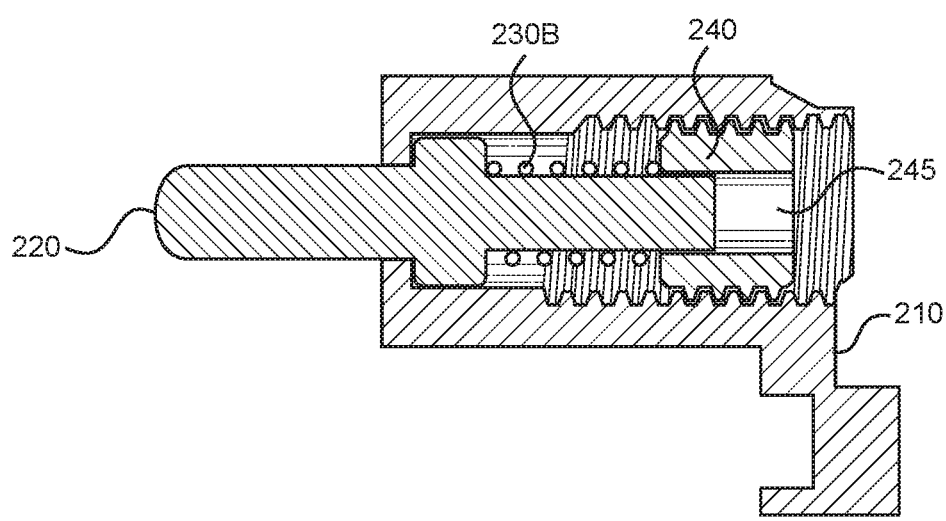
FIG. 9B illustrates a lateral crossectional view of an embodiment of a microneedle impact adjustment device wherein the adjustment nut is in a fully extended position.
Figure 9C:
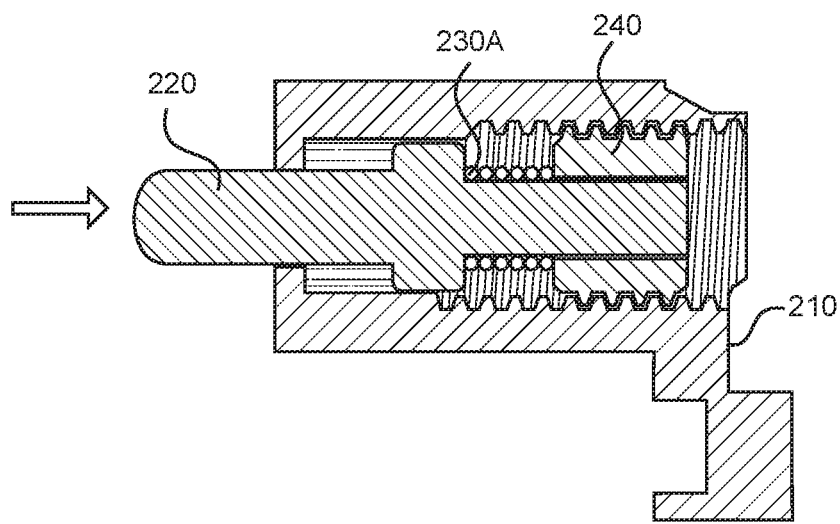
FIG. 9C illustrates a lateral crossectional view of an embodiment of a microneedle impact adjustment device wherein the adjustment nut is in a fully extended position, while the drive pin is under force and the give spring is in a fully compressed position.

FIG. 9 shows a preferred embodiment of a give adjustment and its operation in different settings. FIG. 9A shows the give adjustment in a "hard" setting, with the give nut 240 in its fully inserted position. This causes the give spring to be in a fully compressed state 230A such that the drive pin 220 is in continuous fixed communication with the give slide 210, allowing all force imparted on the give slide by the bellcrank (not shown) to be directly translated to the drive pin without being taken up or absorbed by the give spring. FIG. 9B shows the give adjustment in a "soft" setting with the give nut 240 in its fully extended position. This causes the give spring to be in a low compression state 230B, and thus allows the give spring to be in operational relation between the drive pin 220 and the give nut 240, such that the drive pin 220 is in spring communication with the give slide 210, allowing the drive pin to slidably retract into the give slide, through the give nut slot 245, and compress the give spring whenever the force encountered by the drive pin from a needle (not shown) is greater than the spring force of the give spring. FIG. 9C shows force applied to the drive pin 220, thus compressing the give spring from its extended state until it reaches its fully compressed state 230B whenever sufficient force is applied to the drive pin.

Figure 10:
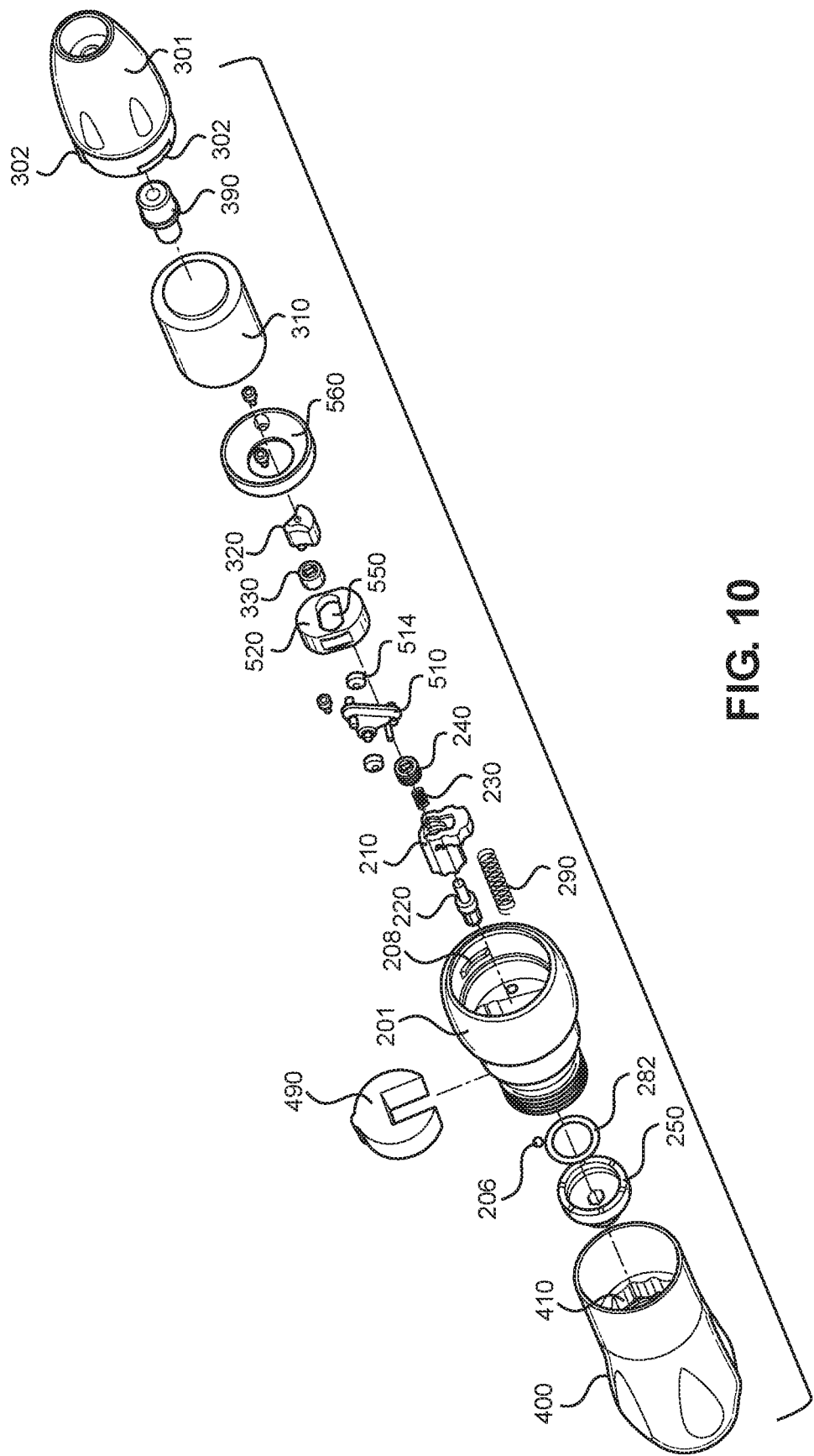
FIG. 10 illustrates an exploded view of an embodiment of a microneedle machine apparatus.

FIG. 10 shows an exploded perspective view of a preferred embodiment of a microneedling apparatus. The motor housing 301 has a plurality of tabs 302 about the circumference of one end. A female RCA adapter is in electrical communication with a motor 310, both of which are fixedly constrained within the motor housing 301. A driveshaft (not visible) of the motor engages a combined counterbalance and offset 320, and the offset engages an offset bearing 330. A follower 520 has a offset bearing groove 550 to accept the offset bearing 330. A bellcrank 510 operably engages the follower 520, and pivotably oscillates about its fulcrum pin and bearings 514 which are fixedly constrained within the give housing 201. A retaining ring 560 constrains the follower inside the give housing. A give nut 240 and give spring 230 are integral to the give slide 210. A drive pin 220 is slidably constrained within the give slide, and rotatably engages the give nut 240. A retraction spring 290 is positioned between the give housing 201 and the give slide 210. The give housing has a plurality of tabs 208 to operably engage the corresponding tabs 302 on the motor housing so that the motor housing and give housing remain in operation relation to each other. The give housing has a press fit ball 206 which engages corresponding detents on the give knob 250. The give knob 250 is reversibly constrained to the give housing 201 by an O-ring 282. The give housing threadingly engages a grip 400. A ratchet disc 490 slottingly engages the give housing 201, and detentingly engages a plurality of grooves 410 integral to the grip 400. The grip 400, give housing 201, and motor housing 301 share a common central axis.

Figure 11:
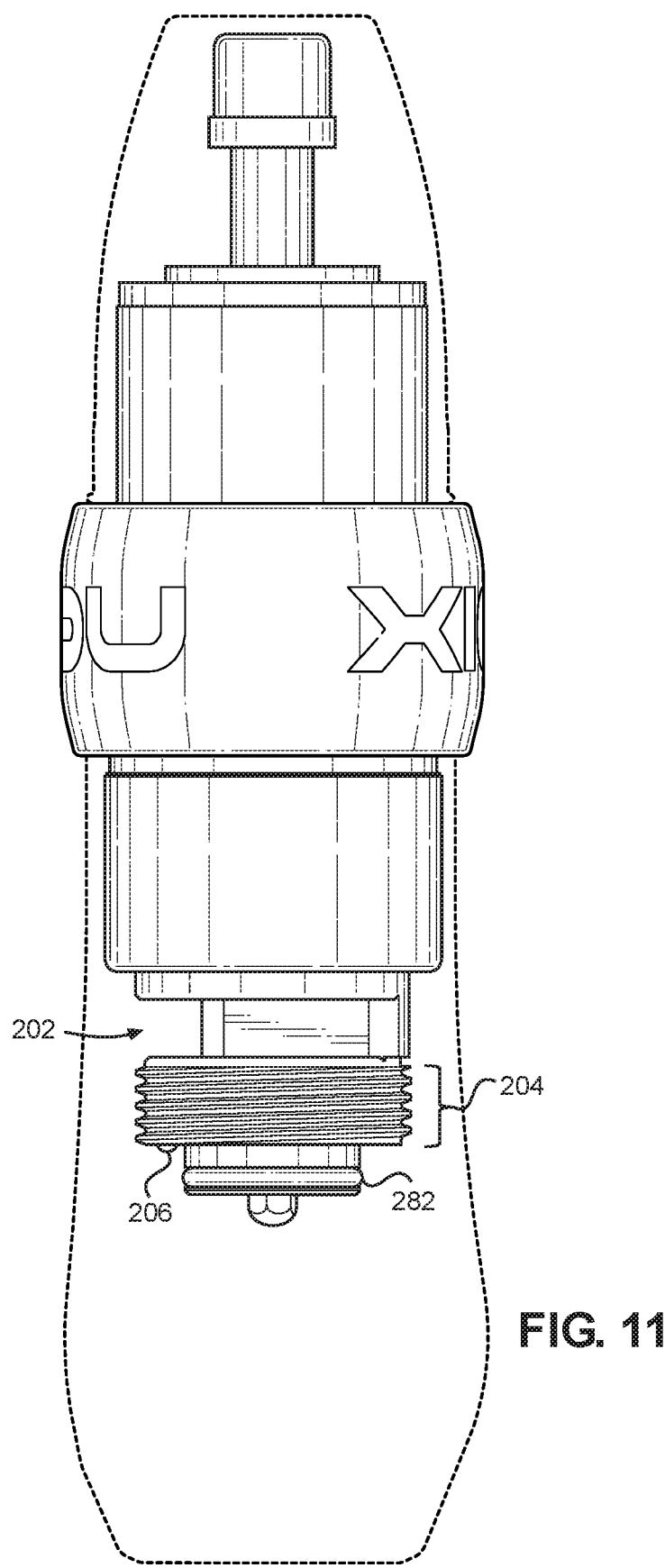
FIG. 11 illustrates a lateral view of an embodiment of a microneedle drive apparatus contained within a grip, and the drive motor contained within a motor housing.

FIG. 11 shows a preferred embodiment of a give housing. The give housing has a slot 202 to accept a ratchet disc (not shown). Threading 204 engages corresponding threads within the grip. One or more balls 206 are provided at the end of the give housing to detentingly engage with corresponding detents on the give knob (not shown). The give knob is reversibly constrained to the give housing through O-ring 282, and thus remains in operational relation to the first end of the drive pin.

Figure 12:
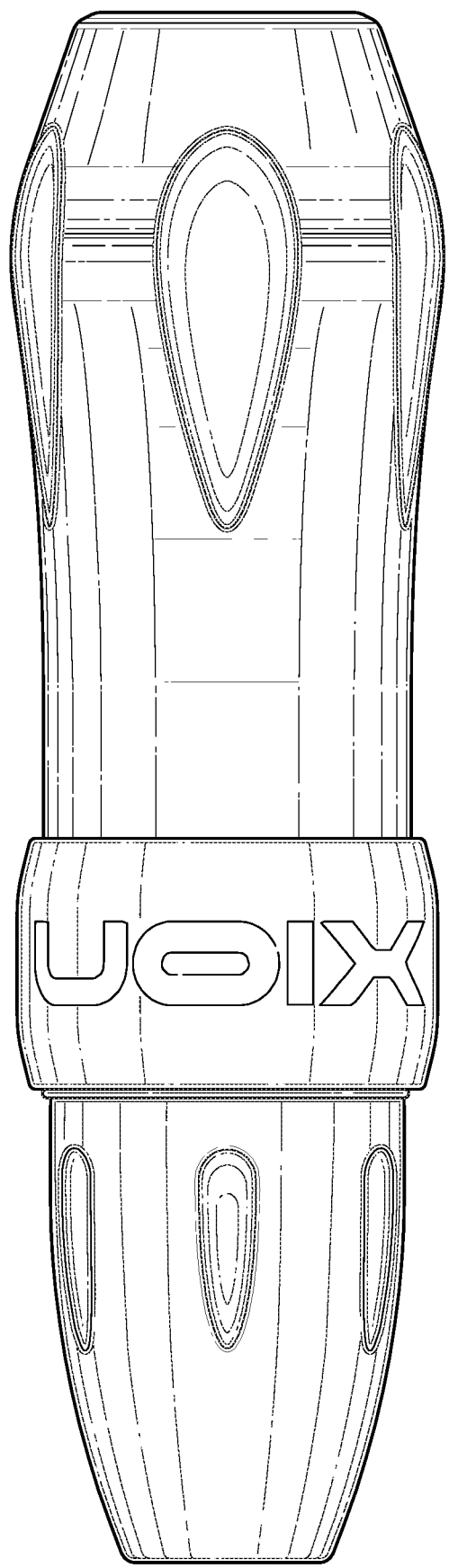
FIG. 12 illustrates a a lateral view of an embodiment of a microneedle machine apparatus.

FIG. 12 shows a side lateral view of a preferred embodiment of a microneedle apparatus, demonstrating a substantially cylindrical device with a common central axis.

In light of the foregoing description, it should be recognized that embodiments in accordance with the present invention can be realized in numerous configurations contemplated to be within the scope and spirit of the claims. Additionally, the description above is intended by way of example only and is not intended to limit the present invention in any way, except as set forth in the claims.

In addition, though the disclosure has been described in reference to several examples optionally incorporating various features, the disclosure is not to be limited to that which is described or indicated as contemplated with respect to each variation of the disclosure. Various changes may be made to the disclosure described and equivalents (whether recited herein or not included for the sake of some brevity) may be substituted without departing from the true spirit and scope of the disclosure. In addition, where a range of values is provided, it is understood that every intervening value, between the upper and lower limit of that range and any other stated or intervening value in that stated range, is encompassed within the disclosure.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present disclosure is not to be limited to the examples provided and/or the subject specification, but rather only by the scope of claim language associated with this disclosure.

What is claimed:

1. A microneedle drive apparatus for converting rotational motion into reciprocating oscillating motion, the microneedle drive apparatus comprising:
   a housing having substantially radial symmetry about a central axis; a rotary motor having an output driveshaft end, the output driveshaft end having an axis of rotation, driveshaft end constrained within the housing and the axis of rotation positioned substantially co-axial to the central axis; and
   a motion translation device dimensioned to fit within the housing comprising an offset comprising a pin, a bearing, and a counterweight, the offset connectable to the driveshaft end wherein the offset is orbitally driven by the driveshaft end a distance from the central axis wherein the offset pin orbits about the central axis as it is driven by the driveshaft end, the counterweight adapted to reduce vibration produced by the mass of the offset as it orbits around the central axis;
   a follower slidingly constrained within the housing and having a first face and a second face, the first face having a groove dimensioned to be engaged by the offset wherein the offset oscillatingly travels within the groove while the follower oscillatingly slides linearly within the housing in a direction orthogonal to the groove as the offset orbits about the driveshaft end;
   a bellcrank having a fulcrum, a first arm, and a second arm, the fulcrum pivotably constrained within the housing, the first arm adapted to be oscillatingly driven by the second face of the follower, wherein the second arm reciprocates as the follower drives the first arm; and
   a ratchet disc having a slot and at least one positive detent, the ratchet disc configured to slottedly mate with the housing, wherein a housing mating portion of a grip of the apparatus has at least one groove parallel to the central axis dimensioned to engage with the at least one positive detent;

wherein the ratchet disc operatively interacts with the at least one groove as the grip is rotated about the central axis relative to the housing.

2. The microneedle drive apparatus of claim 1 wherein the diameter of the housing is between approximately 7 millimeters and approximately 45 millimeters.

3. The microneedle drive apparatus of claim 1, wherein the grip has substantially radial symmetry about the central axis and has a cartridge end and a housing mating portion distal to the cartridge end, the cartridge end dimensioned to accept a microneedle cartridge, the housing mating portion adapted to threadingly engage the housing so that the grip translates onto the housing as the grip is rotated about the central axis relative to the housing.

4. The microneedle machine of claim 1 wherein the offset comprises a bearing and a counterweight adapted to reduce vibration produced by the mass of the offset pin and bearing combination as it orbits around the central axis.

5. The microneedle drive apparatus of claim 1 wherein the follower has a plurality of slide facets that reduce the surface area contact between the follower and the housing for reducing friction as the follower slidingly oscillates within the housing.

6. The microneedle drive apparatus of claim 1 further comprising a spring in mechanical communication between the motion translation device and the housing so as to return the motion translation device to a retracted position.

7. The microneedle drive apparatus of claim 1, further comprising a counterbalance for facilitating a reduction in vibration, heat, or a combination thereof, associated with the microneedle drive apparatus.

8. A microneedle give adjustment apparatus for adjusting the force applied to a microneedle from a drive source, the microneedle give adjustment apparatus comprising:
an adjustment dial having a non-circular aperture through its center;
a give slide comprising a drive end and an inner circumference, the inner circumference defining a substantially cylindrical cavity and having a threaded portion about the inner circumference of the cavity, the drive end having an opening into the cavity;
a drive pin comprising:
a first pin end, the first pin end dimensioned to slidably pass through the opening of the give slide drive end and dimensioned to engage the aperture of the adjustment dial so as to rotatably engage the adjustment dial about the central axis and linearly oscillate through the aperture co-axially with the central axis;
a collar having a diameter larger than the opening of the drive end whereby the collar of the drive pin is retained within the cavity, the collar dimensioned to slide linearly within the cavity; and
a second pin end;
a give nut dimensioned to threadedly engage the give slide cavity and adapted to be rotatably engaged by the second pin end and permit the second pin end to linearly oscillate co-axially with the central axis; and
a spring positioned between the give nut and the collar wherein the spring imparts force between the drive pin and the give nut.

9. The microneedle give adjustment apparatus of claim 8 wherein the give slide has a plurality of slide facets that reduce the surface area contact between the give slide and the housing for reducing friction as the give slide slidingly reciprocates within the housing.

10. A microneedle machine comprising:
a housing having substantially radial symmetry about a central axis;
a motor having a driveshaft and an offset driven by the driveshaft;
a motion translation device dimensioned to fit within the housing comprising
a follower slidingly constrained within the housing and having a first face and a second face, the first face having a groove dimensioned to be engaged by the offset wherein the offset oscillatingly travels within the groove while the follower oscillatingly reciprocates within the housing in a direction orthogonal to the groove as the bearing orbits about the driveshaft; and
a bellcrank having a fulcrum, a first arm, and a second arm, the fulcrum pivotably constrained within the housing, the first arm adapted to be oscillatingly driven by the second face of the follower, wherein the second arm reciprocates as the follower drives the first arm;
a ratchet disc having a slot and at least one positive detent, the ratchet disc configured to slottedly mate with the housing; and
the housing mating portion of the grip having at least one groove parallel to the central axis dimensioned to engage with the at least one positive detent;
wherein the ratchet disc operatively interacts with the at least one groove as the grip is rotated about the central axis relative to the housing.

11. The microneedle give adjustment apparatus of claim 8 further comprising a radially symmetric housing defining a central axis, the adjustment dial, give slide, drive pin, give nut, and spring constrained within an interior of the radially symmetric housing.

12. The microneedle give adjustment apparatus of claim 8 wherein the first pin end is dimensioned to reciprocatingly engage a needle cartridge.

13. The microneedle give adjustment apparatus of claim 11 wherein the first pin end is positioned within the radially symmetric housing coaxially to and concentric with the central axis.

14. The microneedle give adjustment apparatus of claim 11 further comprising a substantially radially symmetric grip, the grip adapted to couple with the radially symmetric housing.

15. The microneedle give adjustment apparatus of claim 8 wherein the give slide further comprises an exterior surface, the exterior surface having one or more facets which reduce the surface area contact between the give slide and an interior of a housing.

16. The microneedle give adjustment apparatus of claim 8 wherein the drive pin first pin end further comprises a plurality of splines, the plurality of splines dimensioned to operatively interact with the non-circular aperture of the adjustment dial.

17. The microneedle give adjustment apparatus of claim 8 wherein the drive pin second pin end further comprises a plurality of splines, the plurality of splines dimensioned to operatively slidingly and rotatingly interact with the give nut.

18. The microneedle give adjustment apparatus of claim 8 wherein the adjustment dial non-circular aperture includes a keyway and the drive pin first pin end further comprises a key dimensioned to operatively interact with the keyway.

19. The microneedle give adjustment apparatus of claim 8 wherein the drive pin second pin end further comprises a key and the give nut further comprises a keyway, the key dimensioned to operatively slidingly and rotatingly interact with the keyway of the give nut.

\* \* \* \* \*